US009625469B2

(12) United States Patent
Marcotte et al.

(10) Patent No.: US 9,625,469 B2
(45) Date of Patent: Apr. 18, 2017

(54) IDENTIFYING PEPTIDES AT THE SINGLE MOLECULE LEVEL

(75) Inventors: Edward Marcotte, Austin, TX (US); Jagannath Swaminathan, Thane (IN); Andrew Ellington, Austin, TX (US); Eric Anslyn, Austin, TX (US)

(73) Assignee: Board Of Regents, The University of Texas System, Austin, TX (US)

( * ) Notice: Subject to any disclaimer, the term of this patent is extended or adjusted under 35 U.S.C. 154(b) by 182 days.

(21) Appl. No.: 14/128,247

(22) PCT Filed: Jun. 22, 2012

(86) PCT No.: PCT/US2012/043769
§ 371 (c)(1),
(2), (4) Date: Apr. 18, 2014

(87) PCT Pub. No.: WO2012/178023
PCT Pub. Date: Dec. 27, 2012

(65) Prior Publication Data
US 2014/0349860 A1    Nov. 27, 2014

Related U.S. Application Data

(60) Provisional application No. 61/500,525, filed on Jun. 23, 2011.

(51) Int. Cl.
*G01N 33/68* (2006.01)
(52) U.S. Cl.
CPC ..... *G01N 33/6824* (2013.01); *G01N 2570/00* (2013.01)
(58) Field of Classification Search
None
See application file for complete search history.

(56) References Cited

U.S. PATENT DOCUMENTS

| | | | |
|---|---|---|---|
| 2008/0242838 A1 | 10/2008 | Peters et al. | 436/86 |
| 2010/0233095 A1 | 9/2010 | Duan et al. | 530/300 |
| 2011/0027300 A1 | 2/2011 | Kamil et al. | 800/3 |
| 2015/0087526 A1* | 3/2015 | Hesselberth | G01N 33/582 506/2 |

FOREIGN PATENT DOCUMENTS

WO    WO/2010/065322    6/2010

OTHER PUBLICATIONS

Oquare, Bereket Yemane, "Design and synthesis of peptide nucleic acid (pna) agents for imaging gene expression." Thesis, Washington University department of Chemistry, Dec. 2007.*
Perron, Y. G. et al, "Derivatives of 6-aminopenicillanic acid. II. Reactions with isocyanates, isothiocyanates, and cyclic anhydrides." J. Org. Chem. (1961) 26(9) p. 3365-3367.*
Cline, Gary W. and Hanna, Samir B., "Kinetics and mechanisms of the aminolyisis of n-hydroxysuccinimide esters in aqueous buffer." J. Org. Chem. (1988) 53 p. 3583-3586.*
The University of Cambridge web page describing the Michaelis-Menten equation, http://www-jmg.ch.cam.ac.uk/tools/magnus/michmenten.html, available online 2009.*
Scangarello, Frank Anthony, "Application of mulivalent displays on metalloprotease-dependent cleavage of semaphorin 4d in synapse development." Thesis, Brandeis University department of Biochemistry, May 2012.*
Tung, Ching-Hsuan et al, "Preparation of a cathepsin d sensitive near-infrared fluorescence probe for imaging." Bioconj. Chem. (1990) 10 p. 892-896.*
The webpage for Nikon microscopes educational literature, https://www.microscopyu.com/references/photobleaching.html, available online Oct. 10, 2010.*
Kelly, Kimberly A. et al, "Targeted nanoparticles for imaging incipient pancreatic ductal adenocarcinoma." PLoS Med. (2008) 5(4) e85.*
The scientist solution forum, http://www.scientistsolutions.com/t11153-keratin+contamination.html, available Jul. 2009.*
Datasheet for I-pentamax camera, Roper Scientific, http://www.spectracore.com/cameras/pdf/ipgeniii.pdf, downloaded Oct. 8, 2015.*
Braslaysky, Ido et al, "Sequence information can be obtained from single dna molecules." PNAS (2003) 100(7) p. 3960-3964.*
Song, Loling et al, "Photobleaching kinetics of fluorescein in quantitative fluorescence microscopy." Biophys. J. (1995) 68 p. 2588-2600.*
Brandt, Mark, "Quenching processes." https://www.rose-hulman.edu/~brandt/Fluorescence/Quenching_processes.pdf, downloaded Feb. 18, 2016.*
Wainaina, Moses N. et al, "Fluroescence detection of amino acids in the postcleavage conversions for manual sequencing of a peptide." Anal. Biochem. (2008) 374 p. 423-425.*
Braslavsky, I. et al. (2003) "Sequence information can be obtained from single DNA molecules," *Proceedings of the National Academy of Sciences* 100(7), 3960-3964.
Edman, P. (1950) "Method for determination of the amino acid sequence in peptides," *Acta Chemica Scandinavica* 4, 283-293.
Edman, P. et al. (1967) "A Protein Sequenator," *European Journal of Biochemistry* 1(1), 80-91.
Harris, T. D. et al. (2008) "Single-Molecule DNA Sequencing of a Viral Genome," *Science* 320(5872), 106-109.

(Continued)

*Primary Examiner* — Fred Reynolds
(74) *Attorney, Agent, or Firm* — Medlen & Carroll, LLP

(57) ABSTRACT

The present invention relates to methods for identifying amino acids in peptides. In one embodiment, the present invention contemplates labeling the N-terminal amino acid with a first label and labeling an internal amino acid with a second label. In some embodiments, the labels are fluorescent labels. In other embodiments, the internal amino acid is lysine. In other embodiments, amino acids in peptides are identified based on the fluorescent signature for each peptide at the single molecule level.

57 Claims, 16 Drawing Sheets

(56) References Cited

OTHER PUBLICATIONS

Niall, H. D. (1973) "Automated Edman degradation: the protein sequenator," *Methods in Enzymology* 27, 942-1010.
Thermo Scientific. (2005) "Thermo Scientific Pierce Cross-Linking Reagents Technical Handbook," 1-48.
PCT International Search Report of International Application No. PCT/US2012/043769 dated Oct. 4, 2012.

* cited by examiner

Structures of Cyanine Dyes Cy3 and Cy5

Scheme for synthesis of Cyanine dyes Cy3 and Cy5

Synthesis of indoles:

Procedures for preparing A, B, C, and D are reported in the literature.

Fluorescently labeled lysines (amine-reactive dye Hilyte 647)
Attached by cysteines to maleimide-PEG quartz surface

SEQUENCE LISTING

```
<160> NUMBER OF SEQ ID NOS: 2

<210> SEQ ID NO 1
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (5)..(8)
<223> OTHER INFORMATION: Xaa can be any naturally occurring amino acid
<220> FEATURE:
<221> NAME/KEY: misc_feature
```

```
<222> LOCATION: (10)..(10)
<223> OTHER INFORMATION: Xaa can be any naturally occurring amino acid

<400> SEQUENCE: 1

Xaa Xaa Xaa Lys Xaa Xaa Xaa Xaa Lys Xaa Lys
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: misc_feature
<222> LOCATION: (10)..(12)
<223> OTHER INFORMATION: Xaa can be any naturally occurring amino acid
<220> FEATURE:
<221> NAME/KEY: MISC_FEATURE
<222> LOCATION: (14)..(14)
<223> OTHER INFORMATION: This X represents any number of intervening
      naturally occurring amino acids between T and C in this amino acid
      labeling pattern.
<220> FEATURE:
<221> NAME/KEY: MISC_FEATURE
<222> LOCATION: (16)..(16)
<223> OTHER INFORMATION: This X represents any number of intervening
      naturally occurring amino acids between C and E in this amino acid
      labeling pattern.

<400> SEQUENCE: 2

Xaa Xaa Xaa Lys Xaa Xaa Xaa Lys Lys Xaa Xaa Xaa Thr Xaa Cys Xaa
1               5                   10                  15
Glu
```

IDENTIFYING PEPTIDES AT THE SINGLE MOLECULE LEVEL

CROSS-REFERENCE TO RELATED APPLICATIONS

The present application claims the benefit of U.S. Provisional Patent Application No. 61/500,525, filed on. Jun. 23, 2011, which is incorporated herein by reference.

This invention was made with government support under R01 GM088624 awarded by The National Institutes of Health. The government has certain rights in the invention.

FIELD OF THE INVENTION

The present invention relates to the field of identifying proteins and peptides, and more specifically large-scale sequencing of single peptides in a mixture of diverse peptides at the single molecule level.

BACKGROUND OF THE INVENTION

The development of Next Generation DNA sequencing methods for quickly acquiring genome and gene expression information has transformed biology. The basis of Next Generation DNA sequencing is the acquisition of large numbers (millions) of short reads (typically 35-450 nucleotides) in parallel. While nucleic acid mutations frequently underlie disease, these changes are most readily embodied by proteins expressed in specific bodily compartments (i.e. saliva, blood, urine) that are accessible without invasive procedures such as biopsies. Unfortunately, a similar high-throughput method for the large-scale identification and quantitation of specific proteins in complex mixtures remains unavailable; representing a critical bottleneck in many biochemical, molecular diagnostic and biomarker discovery assays.

The first method for analysis of the N-terminal amino acid of polypeptides was described by Frederick Sanger, who demonstrated that the free unprotonated α-amino group of peptides reacts with 2,4-dinitrofluorobenzene (DNFB) to form yellow 2,4-dinitrophenyl derivatives (FIG. 1). When such a derivative of a peptide, regardless of its length, is subjected to hydrolysis with 6 N HCl, all the peptide bonds are hydrolyzed, but the bond between the 2,4-dinitrophenyl group and the α-amino of the N-terminal amino acid is relatively stable to acid hydrolysis. Consequently, the hydrolyzate of such a dinitrophenyl peptide contains all the amino acid residues of the peptide chain as free amino acids except the N-terminal one, which appears as the yellow 2,4-dinitrophenyl derivative. This labeled residue can easily be separated from the unsubstituted amino acids and identified by chromatographic comparison with known dinitrophenyl derivatives of the different amino acids.

Sanger's method has been largely supplanted by more sensitive and efficient procedures. An example of one such method employs the labeling reagent 1-dimethylaminoaphthalene-5-sulfonyl chloride (dansyl chloride) (FIG. 2). Since the dansyl group is highly fluorescent, dansyl derivatives of the N-terminal amino acid can be detected and measured in minute amounts by fluorimetric methods. The dansyl procedure is 100 times more sensitive that the Sanger method.

The most widely used reaction for the sequential analysis of N-terminal residue of peptides is the Edman degradation method (Edman et al. "Method for determination of the amino acid sequence in peptides", Acta Chem. Scand. 4: 283-293 (1950) [1], (herein incorporated by reference).

Edman degradation is a method of sequencing amino acids in a peptide wherein the amino-terminal residue is labeled and cleaved from the peptide without disrupting the peptide bonds between other amino acid residues (FIG. 3). In the Edman procedure phenylisothiocyanate reacts quantitatively with the free amino group of a peptide to yield the corresponding phenylthiocarbamoyl peptide. On treatment with anhydrous acid the N-terminal residue is split off as a phenylthiocarbamoyl amino acid, leaving the rest of the peptide chain intact. The phenylthiocarbornyl amino acid is then cyclized to the corresponding phenylthiohydantin derivative, which can be separated and identified, usually by gas-liquid chromatography. Alternatively, the N-terminal residue removed as the phenylthiocarbamoyl derivative can be identified simply by determining the amino acid composition of the peptide before and after removal of the N-terminal residue; called the subtractive Edman method. The advantage of the Edman method is that the rest of the peptide chain after removal of the N-terminal amino acid is left intact for further cycles of this procedure; thus the Edman method can be used in a sequential fashion to identify several or even many consecutive amino acid residues starting from the N-terminal end. Edman and Begg have further exploited this advantage by utilizing an automated amino acid "sequenator" for carrying out sequential degradation of peptides by the phenylisothiocyanate procedure (Eur. J. Biochem. 1:80-91, (1967) [2], (herein incorporated by reference). In one embodiment, such automated amino acid sequencers permit up to 30 amino acids to be accurately sequenced with over 99% efficiency per amino acid (Niall et al. "Automated Edman degradation: the protein sequenator". Meth. Enzymol. 27: 942-1010, (1973) [3], (herein incorporated by reference).

A drawback to Edman degradation is that the peptides being sequenced cannot have more than 50 to 60 (more practically fewer than 30) amino acid residues. The sequenced peptide length is typically limited due to the increase in heterogeneity of the product peptides with each Edman cycle due to cyclical derivitization or cleavage failing to proceed to completion on all peptide copies. Furthermore, since Edman degradation proceeds from the N-terminus of the protein, it will not work if the N-terminal amino acid has been chemically modified or if it is concealed within the body of the protein. In some native proteins the N-terminal residue is buried deep within the tightly folded molecule and is inaccessible. Edman degradation typically is performed only on denatured peptides or proteins. Intact, folded proteins are seldom (if at all) subjected to Edman sequencing.

Importantly, the current automated peptide sequencers that perform Edman degradation cannot sequence and identify individual peptides within the context of a mixture of peptides or proteins. What is thus needed is a massively parallel and rapid method for identifying and quantitating individual peptide and/or protein molecules within a given complex sample.

SUMMARY OF THE INVENTION

The present invention relates to the field of identifying proteins and peptides, and more specifically large-scale sequencing (including but not limited to partial sequencing) of single intact peptides (not denatured) in a mixture of diverse peptides at the single molecule level by selective labeling amino acids on immobilized peptides followed by successive cycles of labeling and removal of the peptides' amino-terminal amino acids. The methods of the present invention are capable of producing patterns sufficiently reflective of the peptide sequences to allow unique identification of a majority of proteins from a species (e.g. the yeast and human proteomes). In one embodiment, the present invention provides a massively parallel and rapid method for identifying and quantitating individual peptide and/or protein molecules within a given complex sample.

In one embodiment, the invention relates to a method of treating peptides, comprising: a) providing a plurality of peptides immobilized on a solid support, each peptide comprising an N-terminal amino acid and internal amino acids, said internal amino acids comprising lysine, each lysine labeled with a first label, said first label producing a first signal for each peptide, and said N-terminal amino acid of each peptide labeled with a second label, said second label being different from said first label; b) treating said plurality of immobilized peptides under conditions such that each N-terminal amino acid of each peptide is removed; and c) detecting the first signal for each peptide at the single molecule level. In one embodiment, said second label is attached via an amine-reactive dye. In one embodiment, said second label is selected from the group consisting of fluorescein isothiocyanate, rhodamine isothiocyanate or other synthesized fluorescent isothiocyanate derivative. In one embodiment, portions of the emission spectrum of said first label do not overlap with the emission spectrum of said second label. In one embodiment, the removal of said N-terminal amino acid in step b) is done under conditions such that the remaining peptides each have a new N-terminal amino acid. In one embodiment, the method further comprises the step d) adding said second label to said new N-terminal amino acids of the remaining peptides. In one embodiment, among the remaining peptides the new end terminal amino acid is lysine. In one embodiment, the method further comprises the step e) detecting the next signal for each peptide at the single molecule level. In one embodiment, the N-terminal amino acid removing step, the detecting step, and the label adding step to a new N-terminal amino acid are successively repeated from 1 to 20 times. In one embodiment, the repetitive detection of signal for each peptide at the single molecule level results in a pattern. In one embodiment, the pattern is unique to a single-peptide within the plurality of immobilized peptides. In one embodiment, the single-peptide pattern is compared to the proteome of an organism to identify the peptide. In one embodiment, the intensity of said first and second labels are measured amongst said plurality of immobilized peptides. In one embodiment, the N-terminal amino acids are removed in step b) by an Edman degradation reaction. In one embodiment, the peptides are immobilized via cysteine residues. In one embodiment, the detecting in step c) is done with optics capable of single-molecule resolution. In one embodiment, the degradation step in which removal of second label coincides with removal of first label is identified. In one embodiment, said removal of the amino acid is measured in step b is measured as a reduced fluorescence intensity.

In one embodiment, the invention relates to a method of treating peptides, comprising: a) providing i) a plurality of peptides immobilized on a solid support, each peptide comprising an N-terminal amino acid and internal amino acids, said internal amino acids comprising lysine, each lysine labeled with a first label, said first label producing a first signal for each peptide, and said N-terminal amino acid of each peptide labeled with a second label, said second label being different from said first label, and ii) an optical device capable of detecting said first collective signal for each peptide at the single molecule level; b) treating said plurality of immobilized peptides under conditions such that each N-terminal amino acid of each peptide is removed; and c) detecting the first signal for each peptide at the single molecule level with said optical device. In one embodiment, said second label is attached via an amine-reactive dye. In one embodiment, said second label is selected from the group consisting of fluorescein isothiocyanate, rhodamine isothiocyanate or other synthesized fluorescent isothiocyanate derivative. In one embodiment, portions of the emission spectrum of said first label do not overlap with the emission spectrum of said second label. In one embodiment, the removal of said N-terminal amino acid in step b) is done under conditions such that the remaining peptides each have a new N-terminal amino acid. In one embodiment, the method further comprises the step d) adding said second label to said new N-terminal amino acids of the remaining peptides. In one embodiment, among the remaining peptides the new end terminal amino acid is lysine. In one embodiment, the method further comprises the step e) detecting the next signal for each peptide at the single molecule level. In one embodiment, the N-terminal amino acid removing step, the detecting step, and the label adding step to a new N-terminal amino acid are successively repeated from 1 to 20 times. In one embodiment, the repetitive detection of signal for each peptide at the single molecule level results in a pattern. In one embodiment, the pattern is unique to a single-peptide within the plurality of immobilized peptides. In one embodiment, the single-peptide pattern is compared to the proteome of an organism to identify the peptide. In one embodiment, the intensity of said first and second labels are measured amongst said plurality of immobilized peptides. In one embodiment, the N-terminal amino acids are removed in step b) by an Edman degradation reaction. In one embodiment, the peptides are immobilized via cysteine residues. In one embodiment, the degradation step in which removal of second label coincides with removal of first label is identified. In one embodiment, said removal of the amino acid is measured in step b is measured as a reduced fluorescence intensity.

In one embodiment, the invention relates to a method of identifying amino acids in peptides, comprising: a) providing a plurality of peptides immobilized on a solid support, each peptide comprising an N-terminal amino acid and internal amino acids, said internal amino acids comprising lysine, each lysine labeled with a first label, said first label producing a first signal for each peptide, and said N-terminal amino acid of each peptide labeled with a second label, said second label being different from said first label, wherein a subset of said plurality of peptides comprise an N-terminal lysine having both said first and second label; b) treating said plurality of immobilized peptides under conditions such that each N-terminal amino acid of each peptide is removed; and c) detecting the first signal for each peptide at the single molecule level under conditions such that said subset of peptides comprising an N-terminal lysine is identified. In one embodiment, the removal of said N-terminal amino acid in step b) is done under conditions such that the remaining peptides each have a new N-terminal amino acid. In one embodiment, the N-terminal amino acids are removed in step b) by an Edman degradation reaction. In one embodiment, the peptides are immobilized via cysteine residues.

In one embodiment, the invention relates to a method of identifying amino acids in peptides, comprising: a) providing a plurality of peptides immobilized on a solid support, each peptide comprising an N-terminal amino acid and internal amino acids, said internal amino acids comprising lysine, each lysine labeled with a first label, said first label producing a first signal for each peptide, and said N-terminal amino acid of each peptide labeled with a second label, said second label being different from said first label, wherein a subset of said plurality of peptides comprise an N-terminal acid that is not lysine; b) treating said plurality of immobilized peptides under conditions such that each N-terminal amino acid of each peptide is removed; and c) detecting the first signal for each peptide at the single molecule level under conditions such that said subset of peptides comprising an N-terminal amino acid that is not lysine is identified. In one embodiment, the removal of said N-terminal amino acid in step b) is done under conditions such that the remaining peptides each have a new N-terminal amino acid. In one embodiment, the N-terminal amino acids are removed in step b) by an Edman degradation reaction. In one embodiment, the peptides are immobilized via cysteine residues.

In one embodiment, the present invention contemplates a method of treating peptides, comprising providing a plurality of peptides immobilized on a solid support, each peptide comprising an N-terminal amino acid and internal amino acids, the internal amino acids comprising lysine, each lysine labeled with a first label, the first label producing a first signal for each peptide (the strength of which will depend in part on the number of labeled lysines for any one peptide), and the N-terminal amino acid of each peptide labeled with a second label, the second label being different from the first label; treating the plurality of immobilized peptides under conditions such that each N-terminal amino acid of each peptide is removed; and detecting the first signal for each peptide at the single molecule level.

In one embodiment, the present invention contemplates a method of treating peptides, comprising providing a plurality of peptides immobilized on a solid support, each peptide comprising an N-terminal amino acid and internal amino acids, the internal amino acids comprising lysine, each lysine labeled with a first label, the first label producing a first signal for each peptide (the strength of which will depend in part on the number of labeled lysines for any one peptide), and the N-terminal amino acid of each peptide labeled with a second label, the second label being different from the first label, and an optical device capable of detecting the first collective signal for each peptide at the single molecule level; treating the plurality of immobilized peptides under conditions such that each N-terminal amino acid of each peptide is removed; detecting the first signal for each peptide at the single molecule level with the optical device.

In one embodiment, the present invention contemplates a method of identifying amino acids in peptides, comprising providing a plurality of peptides immobilized on a solid support, each peptide comprising an N-terminal amino acid and internal amino acids, the internal amino acids comprising lysine, each lysine labeled with a first label, the first label producing a first signal for each peptide (the strength of which will depend in part on the number of labeled lysines for any one peptide), and the N-terminal amino acid of each peptide labeled with a second label, the second label being different from the first label, wherein a subset of the plurality of peptides comprise an N-terminal lysine having both the first and second label; treating the plurality of immobilized peptides under conditions such that each N-terminal amino acid of each peptide is removed; and detecting the first signal for each peptide at the single molecule level under conditions such that the subset of peptides comprising an N-terminal lysine is identified.

In one embodiment, the present invention contemplates a method of identifying amino acids in peptides, comprising providing a plurality of peptides immobilized on a solid support, each peptide comprising an N-terminal amino acid and internal amino acids, the internal amino acids comprising lysine, each lysine labeled with a first label, the first label producing a first signal for each peptide (the strength of which will depend in part on the number of labeled lysines for any one peptide), and the N-terminal amino acid of each peptide labeled with a second label, the second label being different from the first label, wherein a subset of the plurality of peptides comprise an N-terminal acid that is not lysine; treating the plurality of immobilized peptides under conditions such that each N-terminal amino acid of each peptide is removed; and detecting the first signal for each peptide at the single molecule level under conditions such that the subset of peptides comprising an N-terminal amino acid that is not lysine is identified.

In one embodiment, the present invention contemplates a method of treating peptides, comprising providing a plurality of peptides immobilized on a solid support, each peptide comprising an N-terminal amino acid and internal amino acids, the internal amino acids comprising lysine, each lysine labeled with a first label, the first label producing a first signal (e.g. green) for each peptide, and the N-terminal amino acid of each peptide labeled with a second label, the second label being different from the first label, the second label providing a second signal (e.g. red) for each peptide, the first and second signals producing a collective signal (e.g. red/green) for each peptide; detecting the second signal (or the collective signal) for each peptide at the single molecule level; treating the plurality of immobilized peptides under conditions such that each N-terminal amino acid of each peptide is removed; and detecting the first signal for each peptide at the single molecule level.

In one embodiment, the present invention contemplates a method of treating peptides, comprising providing a plurality of peptides immobilized on a solid support, each peptide comprising an N-terminal amino acid and internal amino acids, the internal amino acids comprising lysine, each lysine labeled with a first label, the first label producing a first signal (e.g. green) for each peptide, and the N-terminal amino acid of each peptide labeled with a second label, the second label being different from the first label, the second label providing a second signal (e.g. red) for each peptide, the first and second signals producing a collective signal (e.g. red/green) for each peptide, and an optical device capable of detecting the first and second signal (i.e. either separately or collectively) for each peptide at the single molecule level; detecting the second signal (or the collective signal) for each peptide at the single molecule level with the optical device; treating the plurality of immobilized peptides under conditions such that each N-terminal amino acid of each peptide is removed; and detecting the first signal for each peptide at the single molecule level with the optical device.

In one embodiment, the present invention contemplates a method of identifying amino acids in peptides, comprising providing a plurality of peptides immobilized on a solid support, each peptide comprising an N-terminal amino acid and internal amino acids, the internal amino acids comprising lysine, each lysine labeled with a first label, the first label producing a first signal (e.g. green) for each peptide, and the N-terminal amino acid of each peptide labeled with a second label, the second label being different from the first label, the second label providing a second signal (e.g. red) for each peptide, the first and second signals producing a collective signal (e.g. red/green) for each peptide, wherein a subset of the plurality of peptides comprise an N-terminal lysine having both the first and second label; detecting the second signal (or the collective signal) for each peptide at the single molecule level; treating the plurality of immobilized peptides under conditions such that each N-terminal amino acid of each peptide is removed; and detecting the first signal for each peptide at the single molecule level under conditions such that the subset of peptides comprising an N-terminal lysine is identified.

In one embodiment, the present invention contemplates a method of identifying amino acids in peptides, comprising providing a plurality of peptides immobilized on a solid support, each peptide comprising an N-terminal amino acid and internal amino acids, the internal amino acids comprising lysine, each lysine labeled with a first label, the first label producing a first signal (e.g. green) for each peptide, and the N-terminal amino acid of each peptide labeled with a second label, the second label being different from the first label, the second label providing a second signal (e.g. red) for each peptide, the first and second signals producing a collective signal (e.g. red/green) for each peptide, wherein a subset of the plurality of peptides comprise an N-terminal acid that is not lysine; detecting the second signal (or the collective signal) for each peptide at the single molecule level; treating the plurality of immobilized peptides under conditions such that each N-terminal amino acid of each peptide is removed; and detecting the first signal for each peptide at the single molecule level under conditions such that the subset of peptides comprising an N-terminal amino acid that is not lysine is identified.

In one embodiment, the present invention contemplates a method of sequencing peptides, comprising providing a sample comprising a plurality of peptides, a first label (for example a first fluorescent molecule), and a second label (for example, a second fluorescent molecule); immobilizing the plurality of peptides on a solid support; labeling every residue of a specific amino acid type in the plurality of immobilized peptides with the first label; labeling the N-terminal amino acids of the plurality of immobilized peptides with the second label; removing the N-terminal amino acids of the plurality of immobilized peptides; and detecting the label (for example, measuring the fluorescence intensity of the first and second fluorescent molecules) for single-peptides within the plurality of immobilized peptides. In one embodiment, the labeling and removing steps are successively repeated from 1 to 20 times. In one embodiment, the first and second labels are detected measuring on the plurality of immobilized peptide. In another embodiment, the N-terminal amino acids are removed by an Edman degradation reaction. In another embodiment, the Edman degradation reaction labels the N-terminal amino acids of the immobilized peptides with the second fluorescent molecule. In yet another embodiment, the peptides are immobilized via internal cysteine residues. In one embodiment, the specific amino acid labeled with the first label is lysine. In one embodiment, the first and second labels on the single-peptides are measured with optics capable of single-molecule resolution. In another embodiment, the degradation step in which a loss of second label (for example a reduced fluorescence intensity) coincides with a loss of first label (for example reduced fluorescence intensity) is identified. In one embodiment, the pattern of degradation steps that coincide with a reduction of the first label (for example a loss in fluorescence intensity) is unique to a single-peptide within the plurality of immobilized peptides. In one embodiment, the single-peptide pattern is compared to the proteome of an organism to identify the peptide.

In one embodiment, only a single label is used. In this embodiment, the invention relates to a method of treating peptides, comprising: a) providing a plurality of peptides immobilized on a solid support, each peptide comprising an N-terminal amino acid and internal amino acids, said internal amino acids comprising lysine, each lysine labeled with a label, and said label producing a signal for each peptide; b) treating said plurality of immobilized peptides under conditions such that each N-terminal amino acid of each peptide is removed; and c) detecting the signal for each peptide at the single molecule level. In one embodiment, said label is a fluorescent label. In one embodiment, the removal in step b) said N-terminal amino acid of each peptide reacted with a phenyl isothiocyanate derivative. In one embodiment, the removal of said N-terminal amino acid in step b) is done under conditions such that the remaining peptides each have a new N-terminal amino acid. In one embodiment, the method further comprises the step d) removing the next N-terminal amino acid done under conditions such that the remaining peptides each have a new N-terminal amino acid. In one embodiment, the method further comprises the step e) detecting the next signal for each peptide at the single molecule level. In one embodiment, the N-terminal amino acid removing step and the detecting step are successively repeated from 1 to 20 times. In one embodiment, the repetitive detection of signal for each peptide at the single molecule level results in a pattern. In one embodiment, the pattern is unique to a single-peptide within the plurality of immobilized peptides. In one embodiment, the single-peptide pattern is compared to the proteome of an organism to identify the peptide. In one embodiment, the intensity of said labels are measured amongst said plurality of immobilized peptides. In one embodiment, the N-terminal amino acids are removed in step b) by an Edman degradation reaction. In one embodiment, the peptides are immobilized via cysteine residues. In one embodiment, the detecting in step c) is done with optics capable of single-molecule resolution. In one embodiment, the degradation step in which removal of the N-terminal amino acid coincides with removal of the label is identified. In one embodiment, said removal of the amino acid is measured in step b) is measured as a reduced fluorescence intensity.

DEFINITIONS

To facilitate the understanding of this invention a number of terms are defined below. Terms defined herein (unless otherwise specified) have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, terms defined in the singular are intended to include those terms defined in the plural and vice versa.

As used herein, the term the terms "amino acid sequence", "peptide", "peptide sequence", "polypeptide", and "polypeptide sequence" are used interchangeably herein to refer to at least two amino acids or amino acid analogs that are covalently linked by a peptide bond or an analog of a peptide bond. The term peptide includes oligomers and polymers of amino acids or amino acid analogs. The term peptide also includes molecules that are commonly referred to as peptides, which generally contain from about two (2) to about twenty (20) amino acids. The term peptide also includes molecules that are commonly referred to as polypeptides, which generally contain from about twenty (20) to about fifty amino acids (50). The term peptide also includes molecules that are commonly referred to as proteins, which generally contain from about fifty (50) to about three thousand (3000) amino acids. The amino acids of the peptide may be L-amino acids or D-amino acids. A peptide, polypeptide or protein may be synthetic, recombinant or naturally occurring. A synthetic peptide is a peptide that is produced by artificial means in vitro.

As used herein, the term "fluorescence" refers to the emission of visible light by a substance that has absorbed light of a different wavelength. In some embodiments, fluorescence provides a non-destructive means of tracking and/or analyzing biological molecules based on the fluorescent emission at a specific wavelength. Proteins (including antibodies), peptides, nucleic acid, oligonucleotides (including single stranded and double stranded primers) may be "labeled" with a variety of extrinsic fluorescent molecules referred to as fluorophores. Isothiocyanate derivatives of fluorescein, such as carboxyfluorescein, are an example of fluorophores that may be conjugated to proteins (such as antibodies for immunohistochemistry) or nucleic acids. In some embodiments, fluorescein may be conjugated to nucleoside triphosphates and incorporated into nucleic acid probes (such as "fluorescent-conjugated primers") for in situ hybridization. In some embodiments, a molecule that is conjugated to carboxyfluorescein is referred to as "FAM-labeled".

As used herein, sequencing of peptides "at the single molecule level" refers to amino acid sequence information obtained from individual (i.e. single) peptide molecules in a mixture of diverse peptide molecules. It is not necessary that the present invention be limited to methods where the amino acid sequence information obtained from an individual peptide molecule is the complete or contiguous amino acid sequence of an individual peptide molecule. In some embodiment, it is sufficient that only partial amino acid sequence information is obtained, allowing for identification of the peptide or protein. Partial amino acid sequence information, including for example the pattern of a specific amino acid residue (i.e. lysine) within individual peptide molecules, may be sufficient to uniquely identify an individual peptide molecule. For example, a pattern of amino acids such as X-X-X-Lys-XX-XX-Lys-X-Lys (SEQ ID NO: 1), which indicates the distribution of lysine molecules within an individual peptide molecule, may be searched against a known proteome of a given organism to identify the individual peptide molecule. It is not intended that sequencing of peptides at the single molecule level be limited to identifying the pattern of lysine residues in an individual peptide molecule; sequence information for any amino acid residue (including multiple amino acid residues) may be used to identify individual peptide molecules in a mixture of diverse peptide molecules.

As used herein, "single molecule resolution" refers to the ability to acquire data (including, for example, amino acid sequence information) from individual peptide molecules in a mixture of diverse peptide molecules. In one non-limiting example, the mixture of diverse peptide molecules may be immobilized on a solid surface (including, for example, a glass slide, or a glass slide whose surface has been chemically modified). In one embodiment, this may include the ability to simultaneously record the fluorescent intensity of multiple individual (i.e. single) peptide molecules distributed across the glass surface. Optical devices are commercially available that can be applied in this manner. For example, a conventional microscope equipped with total internal reflection illumination and an intensified charge-couple device (CCD) detector is available (see Braslaysky et al., PNAS, 100(7): 3960-4 (2003) [4]. Imaging with a high sensitivity CCD camera allows the instrument to simultaneously record the fluorescent intensity of multiple individual (i.e. single) peptide molecules distributed across a surface. In one embodiment, image collection may be performed using an image splitter that directs light through two band pass filters (one suitable for each fluorescent molecule) to be recorded as two side-by-side images on the CCD surface. Using a motorized microscope stage with automated focus control to image multiple stage positions in the flow cell may allow millions of individual single peptides (or more) to be sequenced in one experiment.

As used herein, the term "collective signal" refers to the combined signal that results from the first and second labels attached to an individual peptide molecule.

As used herein, the term "subset" refers to the N-terminal amino acid residue of an individual peptide molecule. A "subset" of individual peptide molecules with an N-terminal lysine residue is distinguished from a "subset" of individual peptide molecules with an N-terminal residue that is not lysine.

BRIEF DESCRIPTION OF THE DRAWINGS

For a more complete understanding of the features and advantages of the present invention, reference is now made to the detailed description of the invention along with the accompanying figures.

Figure 1:
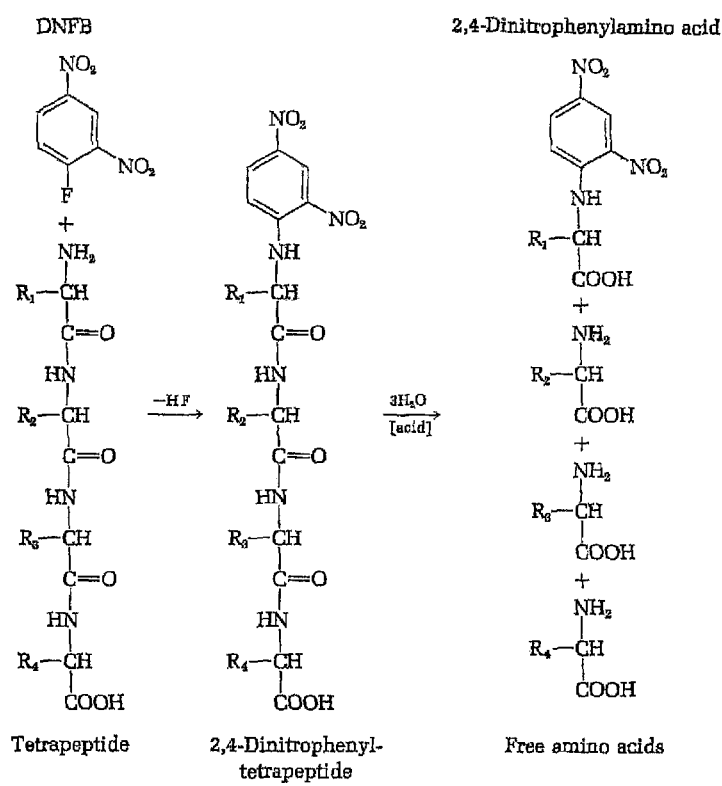
FIG. 1 depicts the identification of the N-terminal amino acid residue of a tetrapeptide by means of the Sanger reaction.
Figure 2:
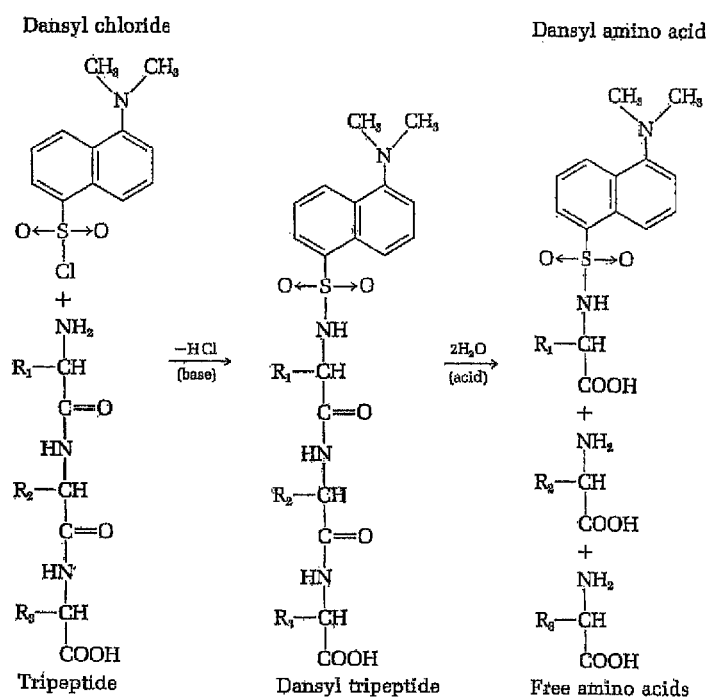
FIG. 2 depicts the identification of the N-terminal residue of a tetrapeptide as the dansyl derivative.
Figure 3:
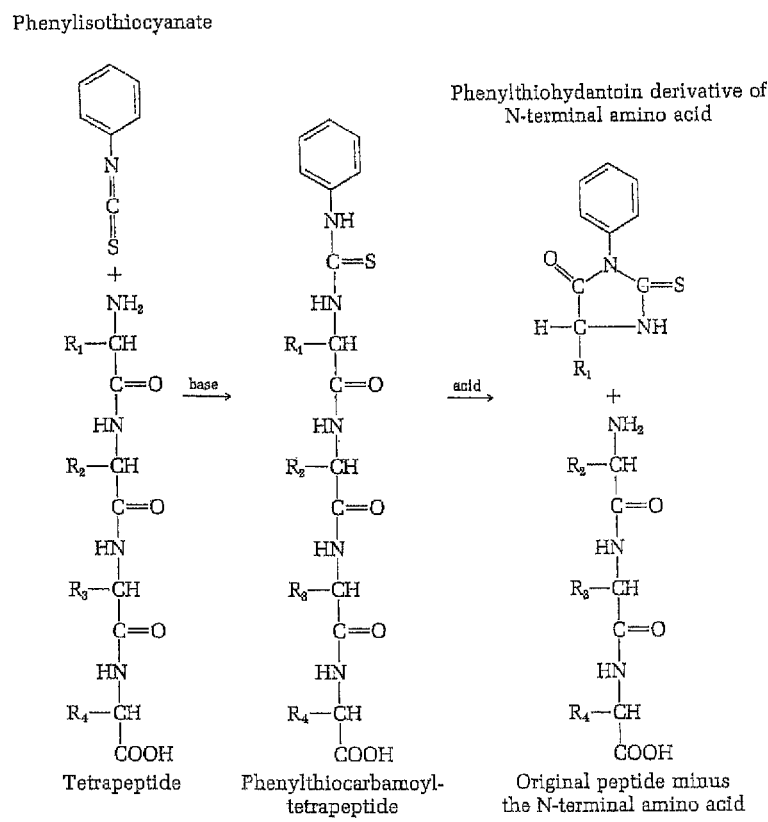
FIG. 3 depicts the identification of the N-terminal amino acid residue by Edman degradation.

Table 1 depicts polypeptide cleavage sites for a number of proteases.

DETAILED DESCRIPTION OF THE INVENTION

The present invention relates to the field of sequencing proteins and peptides, and more specifically large-scale sequencing of single peptides in a mixture of diverse peptides at the single molecule level. In one embodiment, the present application relates to a method to determine protein sequences (including but not limited to partial sequences) in a massively parallel fashion (potentially thousands, and even millions, at a time) wherein proteins are iteratively labeled and cleaved to produce patterns reflective of their sequences. The patterns of cleavage (even of just a portion of the protein) provide sufficient information to identify a significant fraction of proteins within a known proteome, i.e. where the sequences of proteins are known in advance.

I. Protein Sequencing

While changes in nucleic acids often underlie disease, these changes are amplified and are most readily found in proteins, which are in turn present in compartments (i.e. saliva, blood and urine) that are accessible without invasive procedures such as biopsies. Unfortunately, despite advances in high-throughput DNA sequencing, methods for the large-scale identification and quantitation of specific proteins in complex mixtures remain unavailable. For example, a variety of techniques have been examined for identifying unique tumor biomarkers in serum, including mass spectrometry and antibody arrays. However, these techniques are hampered by a lack of sensitivity and by an inability to provide quantitative readouts that can be interpreted with statistical significance by pattern analysis. This deficiency underlies many biochemical assays and molecular diagnostics and represents a critical bottleneck in biomarker discovery.

In one embodiment, the single-molecule technologies of the present application allow the identification and absolute quantitation of a given peptide or protein in a biological sample. This advancement is greater than five orders of magnitude more sensitive than mass spectrometry (the only major competing technology for identifying proteins in complex mixtures), which cannot always accurately quantify proteins because of differential ionization and desorption into the gas phase. Non-limiting example applications might therefore include single molecule detection of circulating proteins in humans or animals, leading to the determination of specific circulating biomarkers for e.g. tumors, infectious disease, etc.

The sequential identification of terminal amino acid residues is the critical step in establishing the amino acid sequence of a peptide. As noted above, a drawback to Edman degradation is that the peptides being sequenced cannot have more than 50 to 60 (more practically fewer than 30) amino acid residues. Peptide length is typically limited because with each Edman cycle there is an incomplete cleavage of the peptides, causing the reaction to lose synchrony across the population of otherwise identical peptide copies, resulting in the observation of different amino acids within a single sequencing cycle. This limitation would however not be applicable to single molecule Edman sequencing such as the method proposed, because the Edman cycling on each peptide is monitored independently.

Amino acids buried within the protein core may not be accessible to the fluorescent label(s), which may give rise to a misleading pattern of amino acids. In one embodiment of the present invention, such derivitization problems may be resolved by denaturing large proteins or cleaving large proteins or large peptides into smaller peptides before proceeding with the reaction.

It was also noted above that, since Edman degradation proceeds from the N-terminus of the protein, it will not work if the N-terminal amino acid has been chemically modified or if it is concealed within the body of the protein. In some native proteins the N-terminal residue is buried deep within the tightly folded molecule and is inaccessible to the labeling reagent. In one embodiment of the present invention the protein or peptide is denatured prior to proceeding with the Edman reaction; in such cases, denaturation of the protein can render it accessible.

It was also noted that while the standard Edman degradation protocol monitors the N-terminal amino acid liberated at each cycle, in one embodiment the present invention monitors the signal obtained from the remaining peptide.

It was also noted that unlike the Edman sequencing traditionally carried out by automated sequenators or sequencers in which complex mixtures of peptides cannot be analyzed, the current invention is capable of identifying individual peptides within a mixture.

II. Fluorescence

Figure 16:
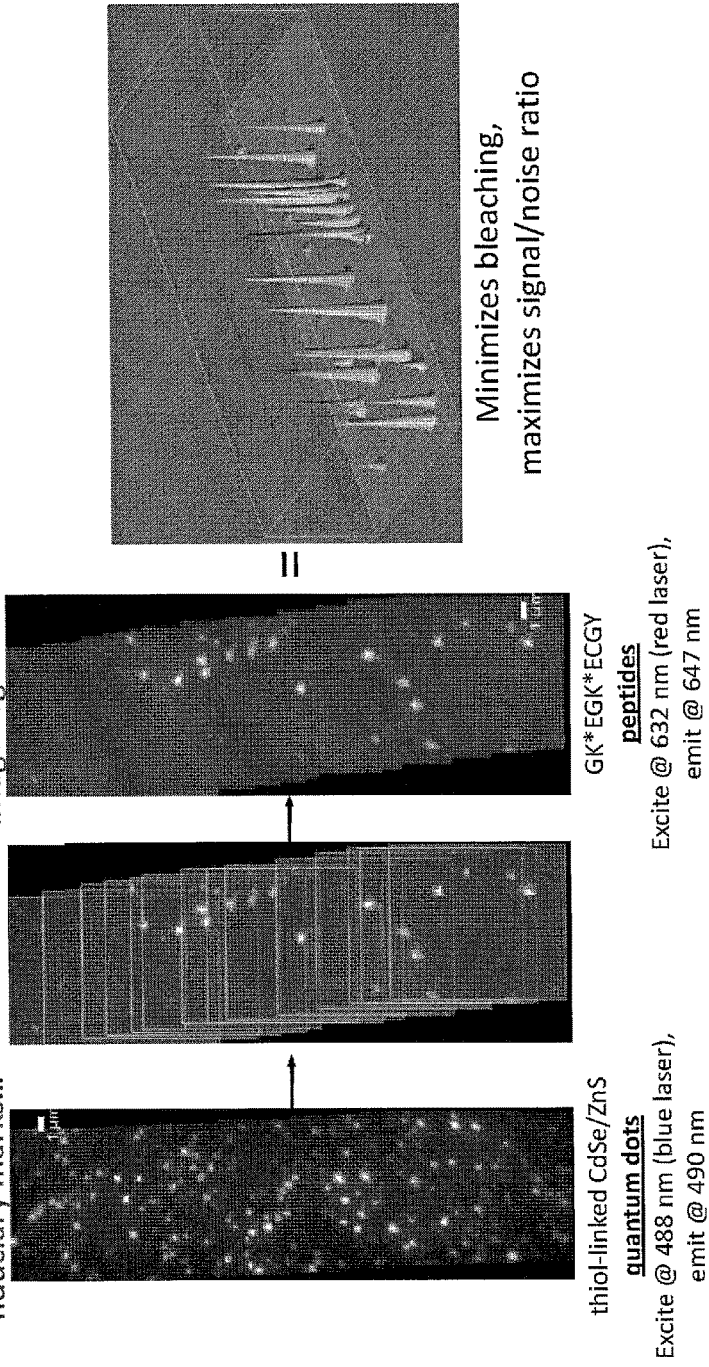
FIG. 16 shows scanning the microscope stage and tiling images to analyze large numbers of peptides wherein quantum dots can serve as guides.

In one embodiment, the first labels utilized in the methods described above is a fluorescent label. In another embodiment, the first and second labels utilized in the methods described above are both fluorescent labels. In the life sciences fluorescence is generally employed as a non-destructive means to track and/or analyze biological molecules since relatively few cellular components are naturally fluorescent (i.e. intrinsic or autofluorescence). Important characteristics of fluorescent peptides are high sensitivity and non-radioactive detection. Fluorescent peptides have been widely used in fluorescence fluorimetry, fluorescence microscopy, fluorescence polarization spectroscopy, time-resolved fluorescence and fluorescence resonance energy transfer (FRET). In general, the preferred fluorescent labels should have high fluorescence quantum yields and retain the biological activities of the unlabeled biomolecules. In one embodiment, a protein can be "labeled" with an extrinsic fluorophore (i.e. fluorescent dye), which can be a small molecule, protein or quantum dot (see FIG. 16). The fluorescent dye may be attached to a peptide at a specific point through a covalent bond, which is stable and not destructive under most physiological conditions. In some embodiments, a functional linker is introduced between the dye and peptide to minimize the alteration of peptide biological activity. Peptide labeling requires attaching the dye at a defined position in the peptide (i.e. N-terminus, C-terminus, or in the middle of sequence).

a) N-Terminal Labeling

Amine-reactive fluorescent probes are widely used to modify peptides at the N-terminal or lysine residue. A number of fluorescent amino-reactive dyes have been developed to label various peptides, and the resultant conjugates are widely used in biological applications. Three major classes of amine-reactive fluorescent reagents are currently used to label peptides: succinimidyl esters (SE), isothiocyanates and sulfonyl chlorides. Fluorescein isothiocyanate (FITC) is one of the most popular fluorescent labeling dyes and is predominantly used for preparing a variety of fluorescent bioconjugates; however, its low conjugation efficiency and short shelf lifetime of FITC conjugates remain troublesome for some biological applications.

i) Fluorescent Dye Carboxylic Acids

Succinimidyl esters (SE) are extremely reliable for amine modifications because the amide bonds that are formed are essentially identical to, and as stable as, the natural peptide bonds. These reagents are generally stable and show good reactivity and selectivity with aliphatic amines. For the most part, reactive dyes are hydrophobic molecules and should be dissolved in anhydrous dimethylformamide (DMF) or dimethylsulfoxide (DMSO). The labeling reactions of amines with succinimidyl esters are strongly pH dependent. Amine-reactive reagents react with non-protonated aliphatic amine groups, including the terminal amines of proteins and the e-amino groups of lysines. Thus amine acylation reactions are usually carried out above pH 7.5. Protein modifications by succinimidyl esters can typically be done at pH 7.5-8.5, whereas isothiocyanates may require a pH 9.0-10.0 for optimal conjugations. Buffers that contain free amines such as Tris and glycine and thiol compounds must be avoided when using an amine-reactive reagent. Ammonium salts (such as ammonium sulfate and ammonium acetate) that are widely used for protein precipitation must also be removed (such as viadialysis) before performing dye conjugations. Most conjugations are done at room temperature. However, either elevated or reduced temperature may be required for a particular labeling reaction.

ii) Fluorescent Dye Sulfonyl Chlorides

Sulfonyl chlorides are highly reactive and are unstable in water, especially at the higher pH required for reaction with aliphatic amines. Molecular modifications by sulfonyl chlorides should be performed at low temperature. Sulfonyl chlorides can also react with phenols (including tyrosine), aliphatic alcohols (including polysaccharides), thiols (such as cysteine) and imidazoles (such as histidine), but these reactions are not common in proteins or in aqueous solution. SC dyes are generally hydrophobic molecules and should be dissolved in anhydrous dimethylformamide (DMF). Sulfonyl chlorides are unstable in dimethylsulfoxide (DMSO) and should never be used in this solvent. The labeling reactions of amines with SC reagents are strongly pH dependent. SC reagents react with non-protonated amine groups. On the other hand, the sulfonylation reagents tend to hydrolyze in the presence of water, with the rate increasing as the pH increases. Thus sulfonylation-based conjugations may require a pH 9.0-10.0 for optimal conjugations. In general, sulfonylation-based conjugations have much lower yields than the succinimidyl ester-based conjugations. Buffers that contain free amines such as Tris and glycine must be avoided when using an amine-reactive reagent. Ammonium sulfate and ammonium must be removed before performing dye conjugations. High concentrations of nucleophilic thiol compounds should also be avoided because they may react with the labeling reagent to form unstable intermediates that could destroy the reactive dye. Most SC conjugations are performed at room temperature, however reduced temperature may be required for a particular SC labeling reaction.

iii) Fluorescent Dye Isothiocyanates

Isothiocyanates form thioureas upon reaction with amines. Some thiourea products (in particular, the conjugates from α-amino acids/peptides/proteins) are much less stable than the conjugates that are prepared from the corresponding succinimidyl esters. It has been reported that antibody conjugates prepared from fluorescein isothiocyanates deteriorate over time. For the most part, reactive dyes are hydrophobic molecules and should be dissolved in anhydrous dimethylformamide (DMF) or dimethylsulfoxide (DMSO). 2). The labeling reactions of amines with isothiocyanates are strongly pH dependent. Isothiocyanate reagents react with nonprotonated aliphatic amine groups, including the terminal amines of proteins and the e-amino groups of lysines. Protein modifications by isothiocyanates may require a pH 9.0-10.0 for optimal conjugations. Buffers that contain free amines such as Tris and glycine must be avoided when using an amine-reactive reagent. Ammonium salts (such as ammonium sulfate and ammonium acetate) that are widely used for protein precipitation must also be removed before performing dye conjugations. High concentrations of nucleophilic thiol compounds should also be avoided because they may react with the labeling reagent to form unstable intermediates that could destroy the reactive dye. Isothiocyanate conjugations are usually done at room temperature; however, either elevated or reduced temperature may be required for a particular labeling reaction.

b) Cyanine Dyes

Figure 8:
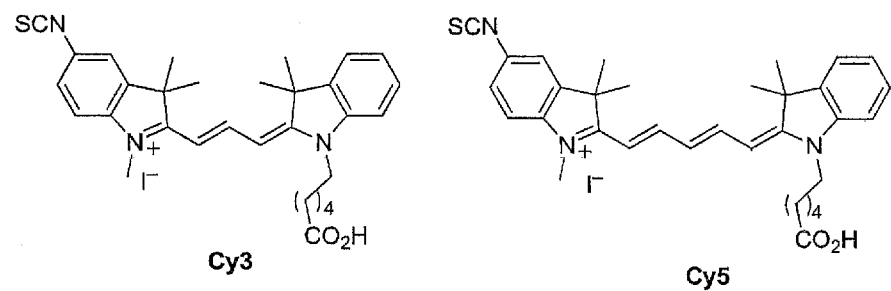
FIG. 8 depicts the structures of cyanine dyes Cy3 and Cy5.
Figure 9:
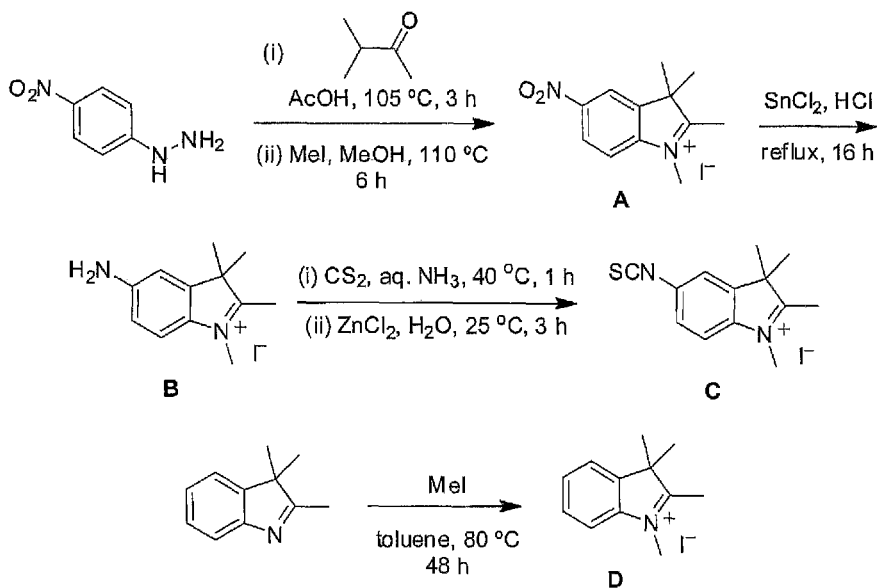
FIG. 9 depicts the synthesis scheme for producing the isothiocyanate derivatives of cyanine dyes Cy3 and Cy5.
Figure 9:
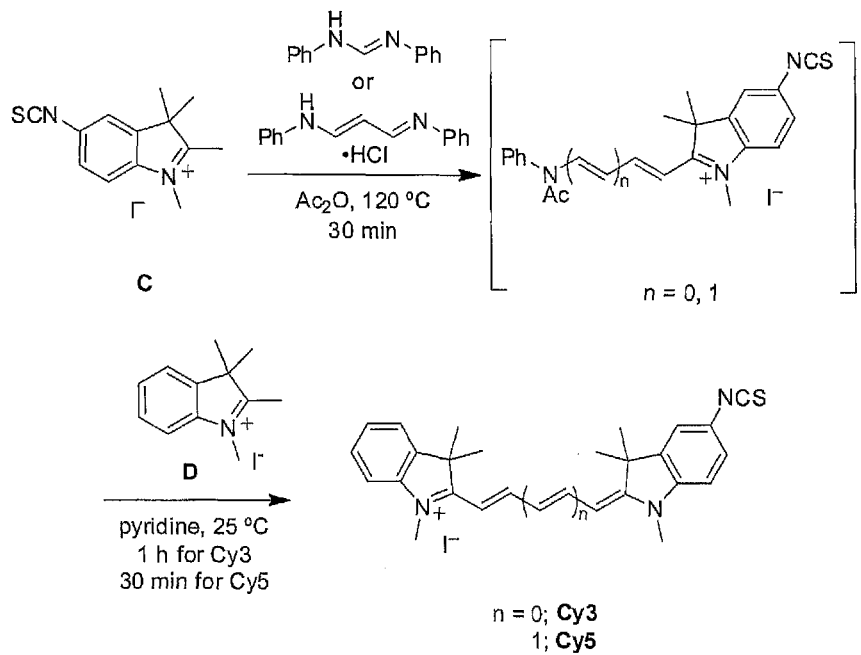

Cyanine dyes exhibit large molar absorptivities (~150,000-250,000M-1 cm-1) and moderate quantum yields resulting in extremely bright fluorescence signals. Depending on the structure, they cover the spectrum from infrared (IR) to ultraviolet (UV). Cyanines have many uses as fluorescent dyes, particularly in biomedical imaging, laser technology and analytical chemistry. Cy3 and Cy5 are reactive water-soluble fluorescent dyes of the cyanine dye family. Cy3 dyes fluoresce in the green-yellow spectrum (~550 nm excitation, ~570 nm emission), while Cy5 dyes fluoresce in the far red spectrum (~650 nm excitation, 670 nm emission) but absorb in the orange spectrum (~649 nm). The chemical structure of both Cy3 and Cy5 is provided in FIG. 8. A detailed synthesis scheme for producing isothiocyanate derivatives of these dyes is also provided (FIG. 9). In one embodiment, Cy3 and Cy5 are synthesized with reactive groups on either one or both of their nitrogen side chains so that they can be chemically linked to either nucleic acids or protein molecules. In one embodiment, this facilitates visualization and/or quantification of the labeled molecule(s). A wide variety of biological applications employ Cy3 and Cy5 dyes, including for example, comparative genomic hybridization and in gene chips, label proteins and nucleic acid for various studies including proteomics and RNA localization.

To avoid contamination due to background fluorescence scanners typically use different laser emission wavelengths (typically 532 nm and 635 nm) and filter wavelengths (550-600 nm and 655-695 nm), thereby providing the ability to distinguish between two samples when one sample has been labeled with Cy3 and the other labeled with Cy5. Scanners are also able to quantify the amount of Cy3 and Cy5 labeling in either sample. In some embodiments, Cy3 and Cy5 are used in proteomics experiments so that samples from two sources can be mixed and run together thorough the separation process. This eliminates variations due to differing experimental conditions that are inevitable if the samples were run separately.

III. Single-Molecule Peptide Identification and Quantitation

In one embodiment, the present application relates to a method to determine protein sequences (typically sequence information for a portion of the protein) in a massively parallel fashion (thousands, and optimally millions at a time) wherein proteins (or fragments/portions thereof) are iteratively labeled and cleaved to produce patterns reflective of their sequences. It is not intended that the present invention be limited to the precise order of certain steps. In one embodiment, the proteins (or peptide fragments thereof) are first labeled and then immobilized, and subsequently treated under conditions such that amino acids are cleaved/removed. In another embodiment, acquiring information about the sequences of single proteins involves two related methods (FIG. 8). Peptides or proteins are first immobilized on a surface (e.g., via internal cysteine residues) and then successively labeled, pieces of the peptides are then cleaved away using either chemical, photochemical or enzymatic degradation. In either case, the patterns of cleavage provide sufficient information to identify a significant fraction of proteins within a known proteome. Given the extraordinary amount of DNA information that has already been accumulated via NextGen DNA sequencing, the sequences of many proteomes are known in advance.

a) Immobilization and Labeling

In one embodiment, peptides or proteins are first immobilized on a surface (via internal cysteine residues), and successively labeled and cleaved away pieces of the peptides based on either chemical or enzymatic degradation (the two variations on the common theme). It is not intended that the present invention be limited to which amino acids are labeled. However, in a preferred embodiment, the chemical methodology entails labeling the lysyl residues of a peptide or protein with a single dye ("green" in FIG. 8). The Edman degradation method is then used to successively cleave amino acid residues away from the amino terminus of the immobilized peptide. In a preferred embodiment, the present application contemplates the use of a modified fluorescent derivative of the Edman reagent in order to successively label each newly exposed residue on the protein ("red" in FIG. 9). This successive labeling permits the efficiency of the reaction to be determined and also "counts" the number of reaction cycles a given immobilized peptide has undergone. Determining when in the "red" count there occurs a coincident loss of "green" residues from a single peptide molecule provides sequence information about that specific peptide. Sequence information resulting from such analysis may be of the form X-X-X-Lys-X-X-X-X-Lys-X-Lys (SEQ ID NO: 1) (for example). In another embodiment, rather than using a fluorescent second label ("red" in FIG. 5), a non-fluorescent Edman reagent such as PITC can be employed instead; in this case, the rounds of Edman cycling are simply counted as they are applied rather than monitoring each optically using the second label.

In a preferred embodiment, the carboxylate side chains of glutamyl/aspartyl residues may be labeled with a third fluorescent molecule (i.e. third color) to further increase the amount of sequence information derived from each reaction. Informatic analyses indicate that performing 20 cycles of Edman degradation in this method is sufficient to uniquely identify at least one peptide from each of the majority of proteins from within the human proteome.

b) Cleavage

In another embodiment, the present application contemplates labeling proteins prior to immobilization followed by the addition of a series of proteases that cleave very specifically between particular amino acid dimers to release the labels. The sequence information obtained by this method may be in the form of patterns such as Lys-[Protease site 1]-Lys-[Protease site 2]-Lys (for example). While it is possible that multiple (or zero) protease sites may exists between given labels, the presence of multiple (or zero) protease sites is also information that can be used to identify a given peptide. As with the Edman degradation reaction, discussed above, informatic analyses reveal that proteases with approximately 20 different dimeric specificities are sufficient to uniquely identify at least one peptide from a substantial fraction of proteins from within the human proteome. In one embodiment, proteases with defined specificities may be generated using directed evolution methods.

c) Identification

A single molecule microscope capable of identifying the location of individual, immobilized peptides is used to "read" the number of fluorescent molecules (i.e. dyes) on an individual peptide in one-dye increments. The level of sensitivity is comparable to that available on commercial platforms, and should allow these subtractive approaches to be successful over several iterations.

As indicated previously, the resulting data does not provide a complete peptide sequence, but rather a pattern of amino acids (e.g. X-X-X-Lys-X-X-X-X-Lys-X-Lys . . . )

(SEQ ID NO. 1) that can be searched against the known proteome sequences in order to identify the immobilized peptide. These patterns sometimes match to multiple peptide sequences in the proteome and thus are not always sufficiently information-rich to unambiguously identify a peptide, although by combining information from multiple peptides belonging to the same protein, the unique identification of proteins could be substantially higher. The present method relies on the fact that potentially millions or billions of immobilized peptides may be sequenced in an analysis (for comparison, current single molecule Next-Gen DNA sequencing can sequence approx. 1 billion reads per run), and thus that a very large proportion of these can be uninformative while still providing sufficient information from the interpretable fraction of peptide patterns to identify and quantify proteins unambiguously.

d) Quantitation

The ability to perform single molecule, high-throughput identification of peptides from complex protein mixtures represents a profound advancement in proteomics. In addition to identifying a given peptide or protein, in one embodiment the present methods also permit absolute quantification of the number of individual peptides from a mixture (i.e. sample) at the single molecule level. This represents an improvement to mass spectrometry, which is greater than 5 orders of magnitude less sensitive and which cannot always accurately quantify proteins because of differential ionization and desorption into the gas phase.

e) Biomarkers

While other techniques have been used to identify unique tumor biomarkers in serum, including mass spectrometry and antibody arrays, these techniques have been greatly hampered by a lack of sensitivity and by an inability to provide quantitative readouts that can be interpreted with statistical significance by pattern analysis. In one embodiment, the present application contemplates the identification of biomarkers relevant to cancer and infectious diseases. While changes in nucleic acids often underlie disease, these changes become typically amplified and are most readily found in proteins. These aberrant proteins are often present in discrete locations throughout the body that are accessible without invasive procedures such as biopsies, including for example, saliva, blood and urine. In one embodiment, a single molecule detection assay for circulating proteins may be performed in a particular animal model of disease (e.g., human proteins from xenografts implanted in mice) to identify unique biomarkers. In a preferred embodiment, such assays may provide the foundation for identifying protein patterns in humans that are indicative of disease. For example, comparing the protein pattern in serum samples from cancer patients versus normal individuals.

Thus, specific compositions and methods of identifying peptides at the single molecule level have been disclosed. It should be apparent, however, to those skilled in the art that many more modifications besides those already described are possible without departing from the inventive concepts herein. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

EXPERIMENTAL

The following are examples that further illustrate embodiments contemplated by the present invention. It is not intended that these examples provide any limitations on the present invention.

In the experimental disclosure that follows, the following abbreviations apply: eq. or eqs. (equivalents); M (Molar); µM (micromolar); N (Normal); mol (moles); mmol (millimoles); µmol (micromoles); nmol (nanomoles); pmoles (picomoles); g (grams); mg (milligrams); µg (micrograms); ng (nanogram); vol (volume); w/v (weight to volume); v/v (volume to volume); L (liters); ml (milliliters); µL (microliters); cm (centimeters); mm (millimeters); µm (micrometers); nm (nanometers); C (degrees Centigrade); rpm (revolutions per minute); DNA (deoxyribonucleic acid); kDal (kilodaltons).

I. Single Molecule Sequencing

Figure 4:
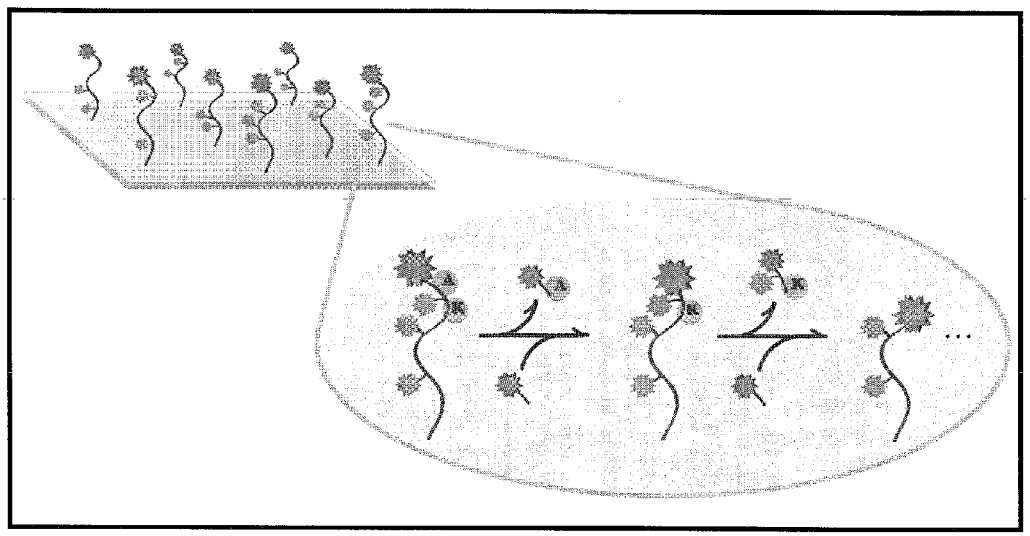
FIG. 4 depicts one embodiment of a single molecule peptide sequencing scheme of the present invention.
Figure 5:
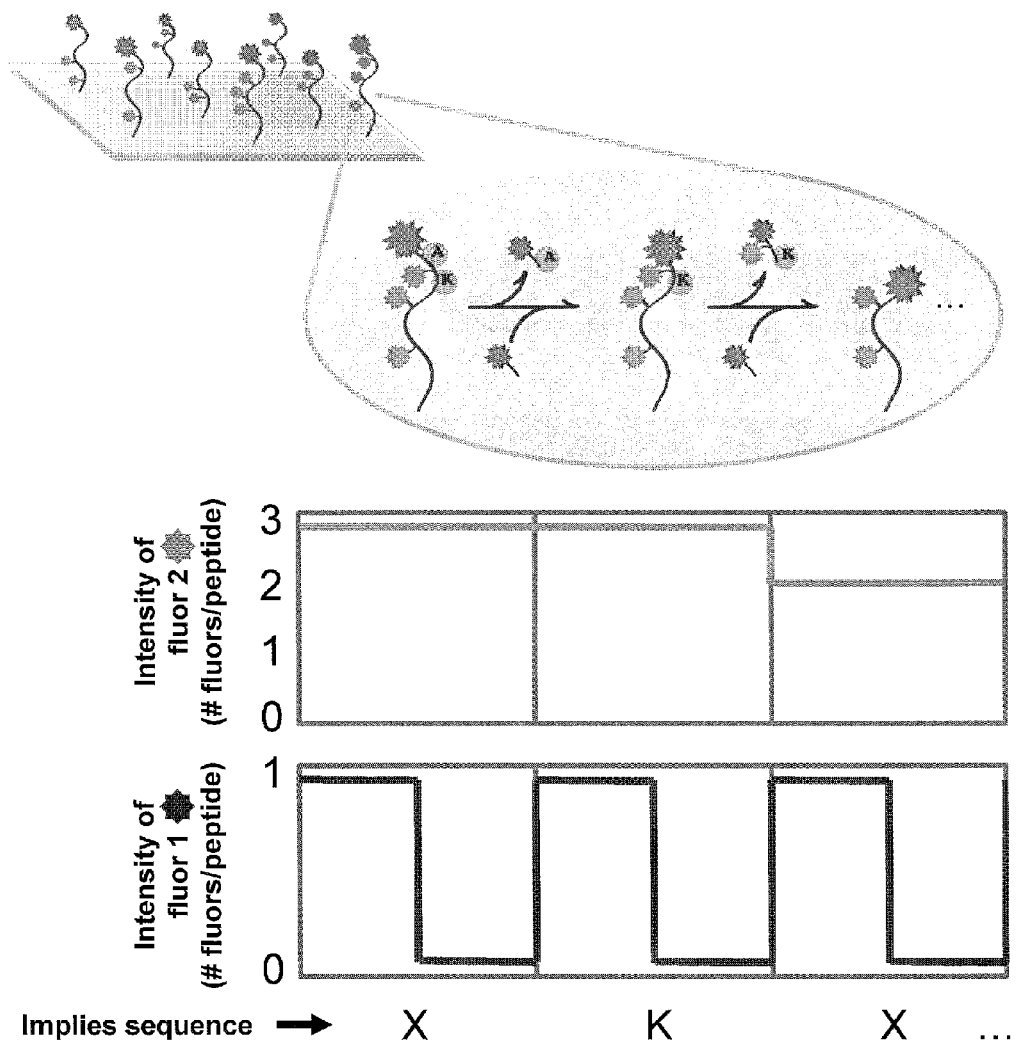
FIG. 5 depicts the selective labeling of immobilized peptides followed by successive cycles of N-terminal amino acid labeling and removal to produce unique patterns that identify individual peptides.

FIG. 4 depicts one embodiment of the single-molecule peptide sequencing method. Briefly, selective labeling of amino acids on immobilized peptides followed by successive cycles of labeling and removal of the peptides' amino-terminal amino acids is capable of producing patterns sufficiently reflective of their sequences to allow unique identification of a majority of proteins in the yeast and human proteomes. FIG. 5 shows the simplest scheme with 2 fluorescent colors (i.e. "fluors" or "labels"), in which fluor 2 (red star) labels the peptide amino termini (N-termini) over successive cycles of removal of the N-terminal amino acids and re-labeling of the resulting new N-termini, and fluor 1 (green star) labels lysine (K) residues. The immobilization of fluor 2 on a peptide serves as an indicator that the Edman reaction initiated successfully; its removal following a solvent change indicates that the reaction completed successfully. Fluor 2 thus serves as an internal error check—i.e., indicating for each peptide which Edman cycles have initiated and completed successfully—and gives a count of amino acids removed from each peptide, as well as reporting the locations of all peptides being sequenced. Fluor 1 serves to indicate when lysines are removed, which, in combination with the reporting of each Edman cycle by fluor 2, gives the resulting sequence profile (e.g. . . . XKX . . . below) that will be used to identify the peptide by comparison with a database of possible protein sequences from the organism being sequenced. In another embodiment, a second fluorescent label is not used; instead, a non-fluorescent version of the reagent which labels and removes the amino termini in successive cycles is employed; in this embodiment, cycles are simply counted, resulting in the same sequence patterns (e.g. . . . XKX . . . ) as in the above embodiment but without providing an internal error check for the successful initiation/completion of each Edman reaction cycle.

a) Identification of Proteins in Yeast and Human Proteomes

Figure 6:
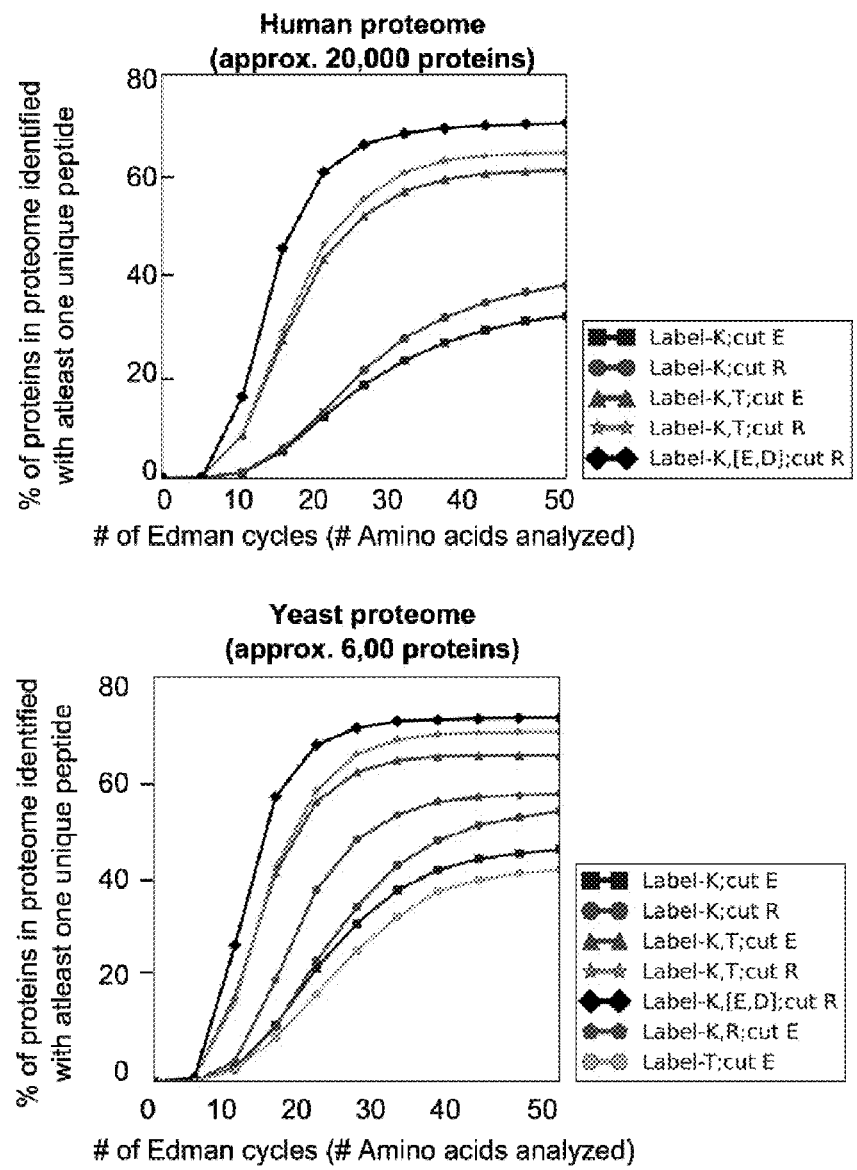
FIG. 6 depicts a simulation that demonstrates that successive cleavage of N-terminal amino acids results in patterns capable of identifying at least one peptide from a substantial fraction of proteins that comprise the human and yeast proteome.

FIG. 6 demonstrates that selective labeling of amino acids on immobilized peptides followed by successive cycles of labeling and removal of their amino-terminal amino acids is capable of producing patterns sufficiently reflective of their sequences to allow unique identification of a majority of proteins in the yeast and human proteomes. Plotted curves show results of computer simulation of successive cleavage of single N-terminal amino acids from all proteolytic peptides derived from the complete human or yeast proteome, top and bottom plots respectively. This figure depicts the results of various cutting ("Cut") and labeling ("Label") scenarios. For example, "Cut E" indicates that all human proteins were proteolyzed with the peptidase GluC in order to cut each protein after glutamate ("E") residues. Similarly, "Label" simulates the results of initially labeling different subsets of amino acid residues. For example, "Label K" indicates that only lysine ("K") amino acid residues carry a detectable label (e.g. a fluorescent molecule observable by single molecule fluorescence microscopy). The sequencing reaction is not allowed to proceed beyond the cysteine ("C") residue since they are used to anchor the peptide sequence. FIG. 5 demonstrates that labeling schemes employing only two or three amino acid-specific fluorescent labels can provide patterns capable of uniquely identifying at least one peptide from a substantial fraction of the human or yeast proteins. Given that only one peptide is required to identify the presence of an individual protein in a protein mixture, and further given that the peptide may be observed repeatedly and the number of observations counted, FIG. 6 demonstrates that this approach may both identify and quantify a large proportion of proteins in highly complex protein mixtures. This capability requires that the genomic sequence of the organism being analyzed is available to serve as a reference for the observed amino acid patterns.

As indicated above, the complete human and yeast genomes are available to match against patterns of amino acid labels (e.g. "XXXKXXXKKXXXTX . . . C . . . E") (SEQ ID NO: 2).

b) Lysine Content

Figure 7:
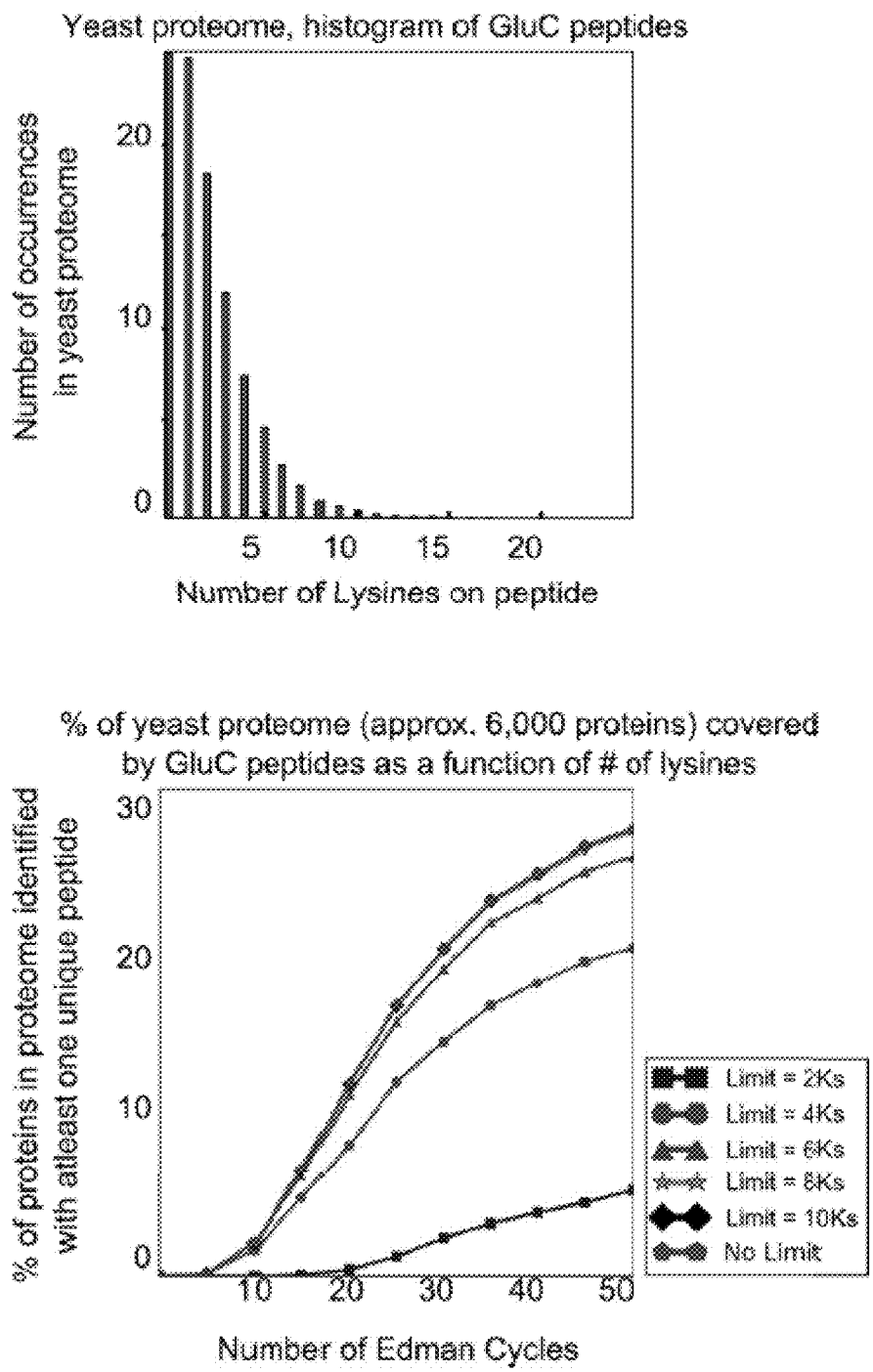
FIG. 7 depicts a simulation that demonstrates that limiting sequencing to peptides with no more than eight lysines provides nearly the coverage of the full set of peptides in the yeast proteome.

FIG. 7 demonstrates that the numbers of lysines per peptide are sufficiently low to monitor their count based on fluorescence intensity. The present method requires the ability to distinguish (i.e. resolve) different numbers of fluorescent molecules based on fluorescence intensity; however, resolution naturally decreases as the number of lysines in a single peptide increase. For example, while distinguishing 3 lysines from 2 lysines only requires detecting a 33% decrease in fluorescence intensity, high lysine counts would require detecting proportionally smaller changes in fluorescence intensity (e.g. only 5% for the case of 21 lysines versus 20 lysines). Fortunately, the natural distribution of lysine residues in peptides tends to be small (top plot, shown for the yeast proteome), and therefore within the capacity of current fluorescent microscopes. The simulations depicted in FIG. 7 demonstrate that limiting sequencing to peptides with no more than eight lysines nearly provides coverage for the full set of peptides in the yeast proteome (bottom plot, shown for the case of labeling K, cutting at E with GluC, anchoring by C).

II. Two-Color Single-Molecule Peptide Sequencing Reaction

Proteins may be analyzed from natural or synthetic sources collected using standard protocols. For example, proteins may be isolated from human cells obtained from blood samples, tumor biopsies or in vitro cell cultures. In one embodiment, the present invention contemplates a two-color single molecule peptide sequencing reaction. In other embodiments, protein sequencing protocols may include more than two fluorescent molecules (e.g. covalently labeling a third fluorescent molecule with an additional type of amino acid) to provide greater protein sequence and/or protein profile information.

a) Cell Sample Preparation

Isolated cells are resuspended in a standard lysis buffer that includes a reducing agent such as Dithiothreitol (DTT) to denature proteins and break disulphide linkages and a protease inhibitor cocktail to prevent further protein degradation. Cells are lysed by homogenization or other lysis technique and the lysate centrifuged to obtain soluble cytosolic proteins (supernatant) and insoluble membrane bound proteins (pellet). Samples may be further fractionated, e.g. by chromatography, gel electrophoresis, or other methods to isolate specific protein fractions of interest. The protein mixtures are denatured in a solution containing, for example, urea or trifluoroethanol (TFE) and the disulfide bonds are reduced to free thiol group via the addition of reducing agents such as tris(2-carboxyethyl)phosphine (TCEP) or DTT.

b) Protein Digestion, Labeling and Anchoring

Protein preparations are then digested by specific endopeptidases (e.g. GluC), which selectively cleave the peptide bonds' C-terminal to glutamic acid residue. The resulting peptides are labeled by a fluorescent Edman reagent (label 1) such as fluorescein isothiocyanate (FITC), rhodamine isothiocyanate or other synthesized fluorescent isothiocyanate derivative (e.g., Cy3-ITC, Cy5-ITC). Considerations in choosing the first fluorescent Edman reagent (label 1) include 1) good reactivity towards available amine groups on Lysine residues and the N-terminus, 2) high quantum yield of the fluorescent signal, 3) reduced tendency for fluorescent quenching, and 4) stability of the fluorescent molecule across the required range of pH.

Labeled peptides are then anchored to an activated glass or quartz substrate for imaging and analysis. In one embodiment, the substrate is glass coated with a low density of maleimide, which is chemically reactive to available sulfydryl groups (SH—) on the cysteine residues in a subset of the peptide molecules. In a preferred embodiment, the substrate is glass coated with a layer of N-(2-aminoethyl)-3-aminopropyl trimethoxy silane and then passivated with a layer of methoxy-poly(ethylene glycol) doped with 2-5% maleimide-poly(ethylene glycol), the latter of which is chemically reactive to available sulfhydryl groups (SH—) on the cysteine residues in a subset of the peptide molecules. In this embodiment only peptides that contain cysteine residues are anchored to the solid surface; peptides that do not contain cysteine residues are washed away in successive steps. In a preferred embodiment, peptides are preferably anchored with a surface density that is low enough to permit the resolution of single molecules during subsequent microscopy steps. In one embodiment, the order of the labeling and anchoring steps may be reversed, for example if required by the coupling-decoupling rate of the Edman reagent and its ability to produce thioazolinone N-terminal amino acid derivatives.

c) Edman Sequencing in a Microscope Flow Cell

Figure 10:
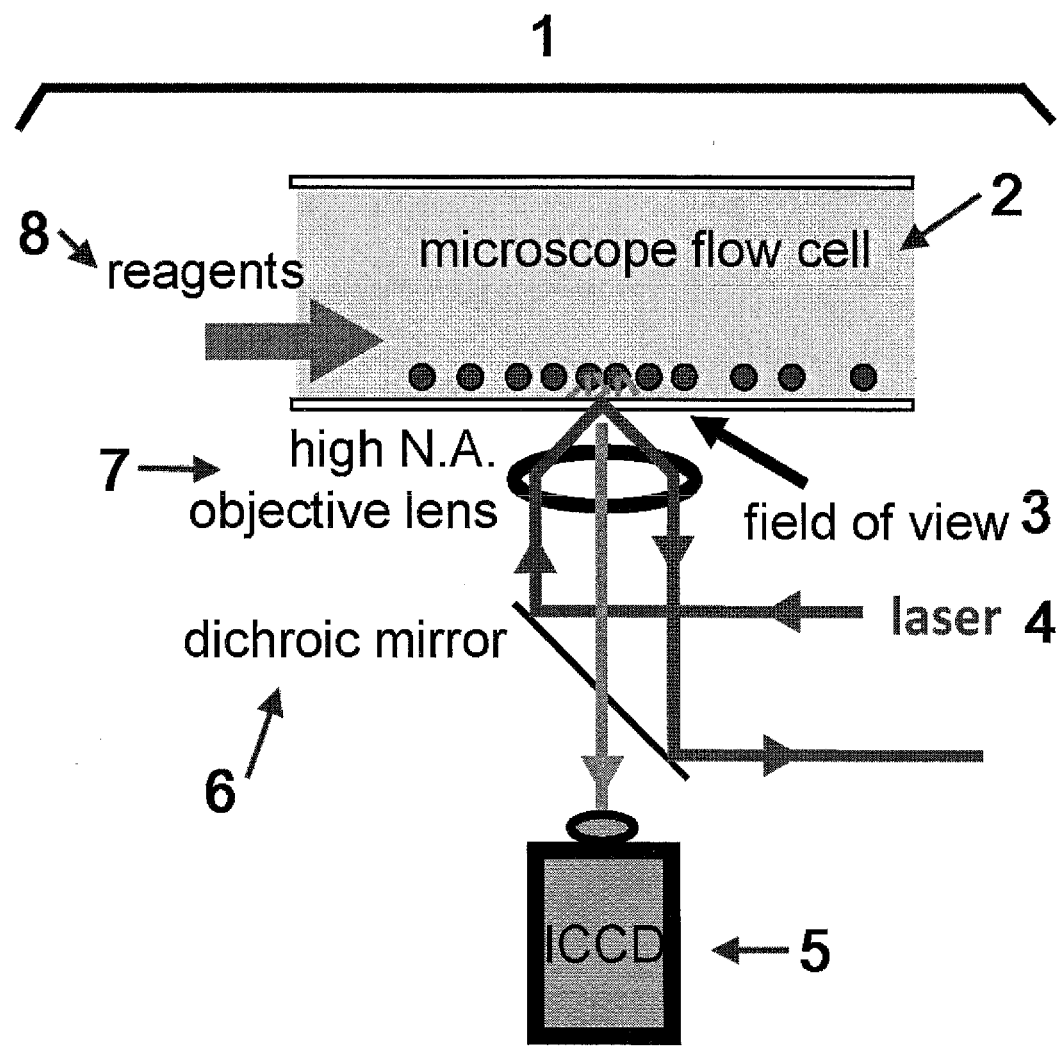
FIG. 10 shows one diagram of a total internal reflectance fluorescence (TIRF) microscopy setup (1) that can be used in one embodiment of sequence analysis. In such a setup is a microscope flow cell (2) wherein the fluorescence of the labeled proteins can be observed through the field of view (3). The laser (4) is directed against the dichroic mirror (6) through the high numerical aperture objective lens (7) through the field of view (3). An intensified charge-couple device (ICCD) (5) observes the fluorescent signal from the labeled peptides.
Figure 11:
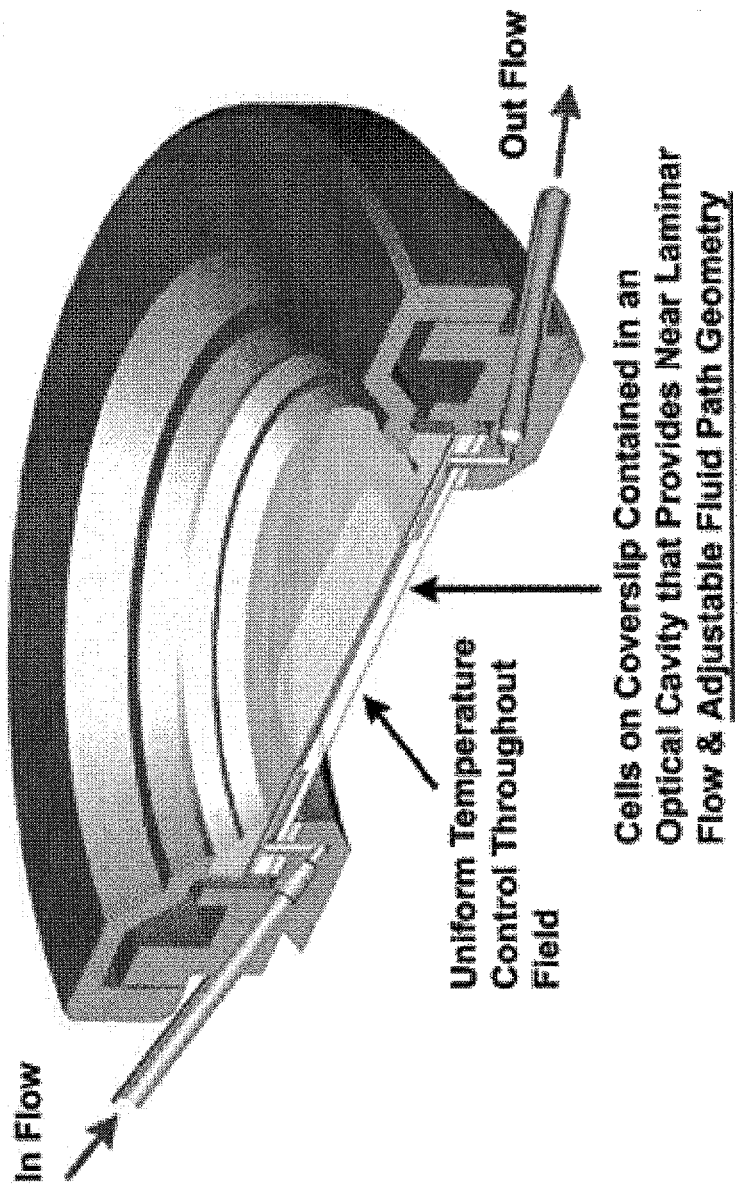
FIG. 11 shows a cross-sectional view of one embodiment of a closed perfusion chamber flow cell. Modifications to this commercial flow cell are to the materials employed for the lower gasket, for which many materials have been tested and are currently using Teflon in order to be resistant to the solvents used for the Edman procedure, and to the surface of the glass slide, which we modify chemically in order to immobilize the peptides.
Figure 12:
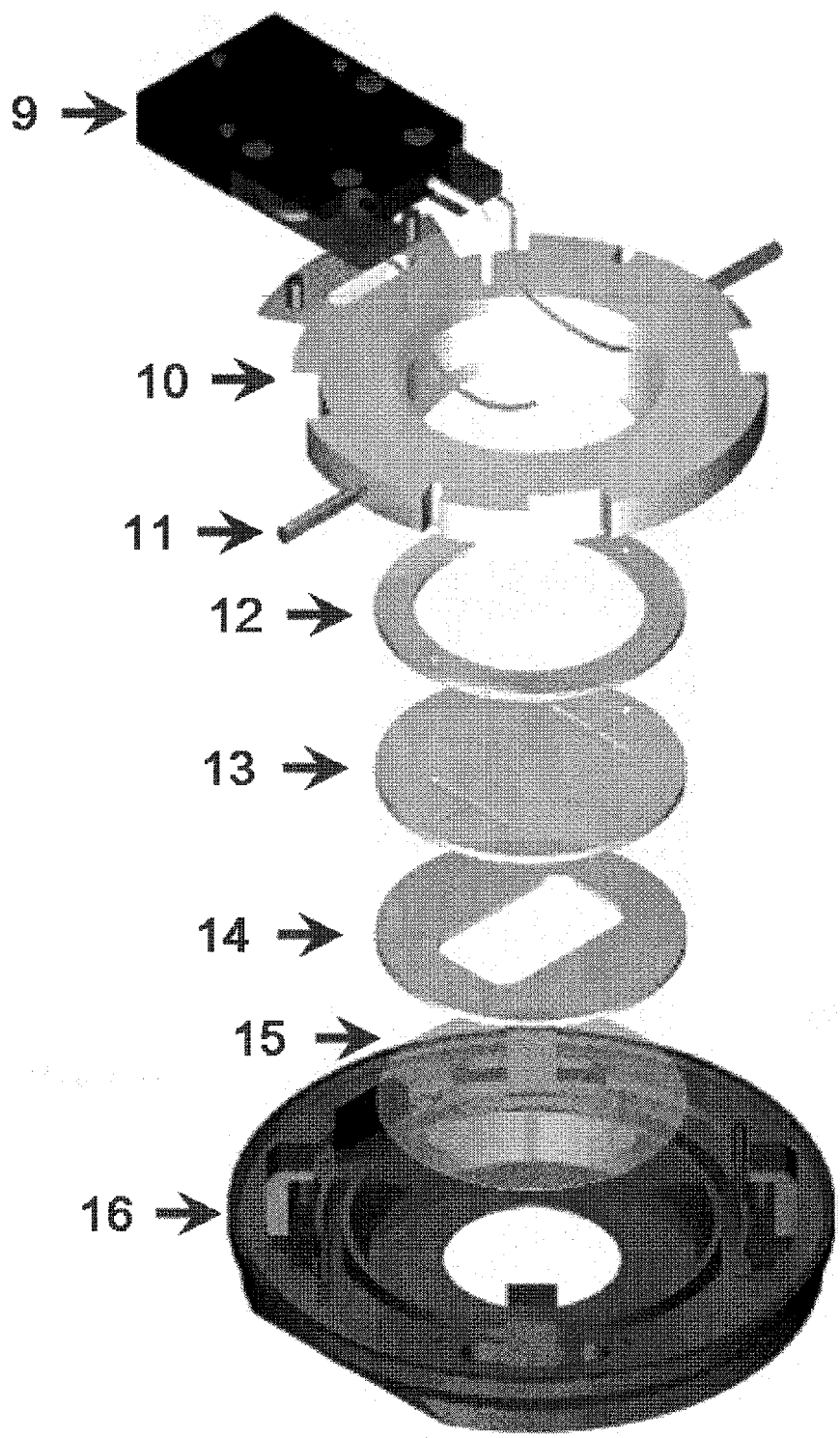
FIG. 12 shows an exploded view of one embodiment of a closed imaging chamber. In this embodiment, the closed imaging chamber includes: Electrical Enclosure (9) which can be detached to sterilize the perfusion tubes an contains temperature sensor and heater contacts; flow cell chamber top (10)—Designed to assure parallel uniform closure, eliminate leaks, and broken coverslips and contains the perfusion tubes; Perfusion Tubes (11) For fluid flow; Upper gasket (12); Flow Control/Microaqueduct Slide (13)—An optical surface which integrates perfusion and temperature control, High-volume laminar flow, Koehler illumination, and electronically conductive coating for temperature control; Lower Gasket (14)—Provides a seal between the flow cell coverslip and flow control slide. This gasket can have any internal geometry one desires. Standard thicknesses from 0.1 mm to 1.0 mm are contemplated. This allows one to define the volume and flow characteristics of the chamber. Modifications to this commercial flow cell are to the materials employed for the lower gasket (14), for which many materials have been tested and are currently using Teflon in order to be resistant to the solvents used for the Edman procedure, and to the surface of the glass slide, which we modify chemically in order to immobilize the peptides; Coverslip (15); and flow cell stage adapter base (16)—Temperature controlled and contains a dovetail to lock into stage adapter for stability. In one non-limiting implementation, a teflon lower gasket is preferrably employed (14) in order to allow for the use of organic solvents in the flow cell.

Following labeling and anchoring of the peptides the substrate (e.g., glass slide) is introduced into a flow cell in a fluorescence microscope equipped with total internal reflection illumination, which reduces background fluorescence. The flow cell is washed with purified water to clean the surface. Steps 2 and 3 correspond to the Edman coupling steps, which are performed repeatedly with fluorescence microscopy images collected twice in each cycle—once after cleavage and once after re-labeling. FIG. 10 is a diagram showing one embodiment of the working principle of a total internal reflectance fluorescence (TIRF) microscopy setup that can be used in sequence analysis. Other embodiments of the microscopy setup include the use of a scanning confocal microscope for visualizing the single molecules or a dove prism for performing TIRF. Using a motorized microscope stage with automated focus control to image multiple stage positions in the flow cell may allow millions of individual single peptides (or more) to be sequenced in one experiment (see FIG. 10, FIG. 11, and FIG. 12).

In the cleavage step trifluoroacetic acid (TFA) is introduced into the flow cell and incubated to complete the cleavage reaction. The liberated thiazolinone N-terminal amino acid derivative and residual TFA is washed away with an organic solvent such as -ethyl acetate. In a preferred embodiment, other solvents may be used to ensure that side products produced are effectively removed. In the re-labeling step the N-terminus of the anchored peptides is re-labeled with a second Edman fluorescent reagent (label 2) under mildly basic conditions. Considerations in choosing the second Edman fluorescent reagent (label 2) include limiting fluorescence bleedthrough (spectral crossover) with label 1 by selecting fluorophores having well-separated absorption and emission spectra such that the fluors can be independently observed via microscopy, and having an efficient rate of decoupling from the labeled N-terminal amino acid. In one embodiment, portions of the emission spectrum of said first label do not overlap with the emission spectrum of said second label. The cleavage and re-labeling steps (steps 2 and 3, respectively) are then repeated in cycles (i.e., treating peptides to the successive rounds of Edman chemistry, involving TFA wash, vacuum dry, etc.) with fluorescence microscopy imaging at each step, as described below, until sufficient data is collected (e.g., 20 or 30 cycles).

d) Single Molecule Fluorescence Microscopy

In one embodiment, a conventional microscope equipped with total internal reflection illumination and an intensified charge-couple device (CCD) detector may be used for imaging. (For an example of such a scope appropriate for single molecule imaging, see Braslaysky et al., PNAS, 100(7): 3960-4 (2003) [4], (herein incorporated by reference). Depending on the absorption and emission spectra of the two fluorescent Edman labels employed, appropriate filters (for example, a central wavelength of 515 nm for FITC and 630 nm for a rhodamine-ITC derivative) are used to record the emission intensity of the two labels. Imaging with a high sensitivity CCD camera allows the instrument to simultaneously record the fluorescent intensity of multiple single peptide molecules distributed across the glass surface. In one embodiment, image collection is performed using an image splitter that directs light through two band pass filters (one suitable for each fluorescent molecule) to be recorded as two side-by-side images on the CCD surface. FIG. 10 is a diagram showing one embodiment of a total internal reflectance fluorescence (TIRF) microscopy setup that can be used in sequence analysis. Using a motorized microscope stage with automated focus control to image multiple stage positions in the flow cell may allow millions of individual single peptides (or more) to be sequenced in one experiment (see FIG. 10, FIG. 11, and FIG. 12). By way of comparison, current generation single molecule DNA sequencers (e.g., available from Helicos) can sequence approximately 1 billion single DNA molecules per experiment.

As described above, for each Edman cycle the fluorescence intensity of label 1 will be recorded after each cleavage step. After the very first round of removal of label 1 (which corresponds to removing the labeled N-terminal amino acid), this label will exclusively label lysine residues in the immobilized peptides, with a fluorescence intensity proportional to the count of lysines in a given peptide. The loss and uptake of label 2 measured after each cleavage step and coupling step, respectively, serves as 1) a counter for the number of amino acid residues removed, and 2) an internal error control indicating the successful completion of each round of Edman degradation for each immobilized peptide.

e) Bioinformatic Analysis

Following image processing to filter noise and identify the location of peptides, as well as to map the locations of the same peptides across the set of collected images, intensity profiles for label 1 and label 2 are associated with each peptide as a function of Edman cycle. The label 1 intensity profile of each error free peptide sequencing reaction (determined by the cycling of label 2) is transformed into a binary sequence (e.g., 00010001100) in which a "1" precedes a drop in fluorescence intensity of label 1 and its location (i.e. position within the binary sequence) identifies the number of Edman cycles performed. This sequence, termed the binary intensity profile, represents a simplified version of the experimentally derived peptide sequence.

Figure 13:
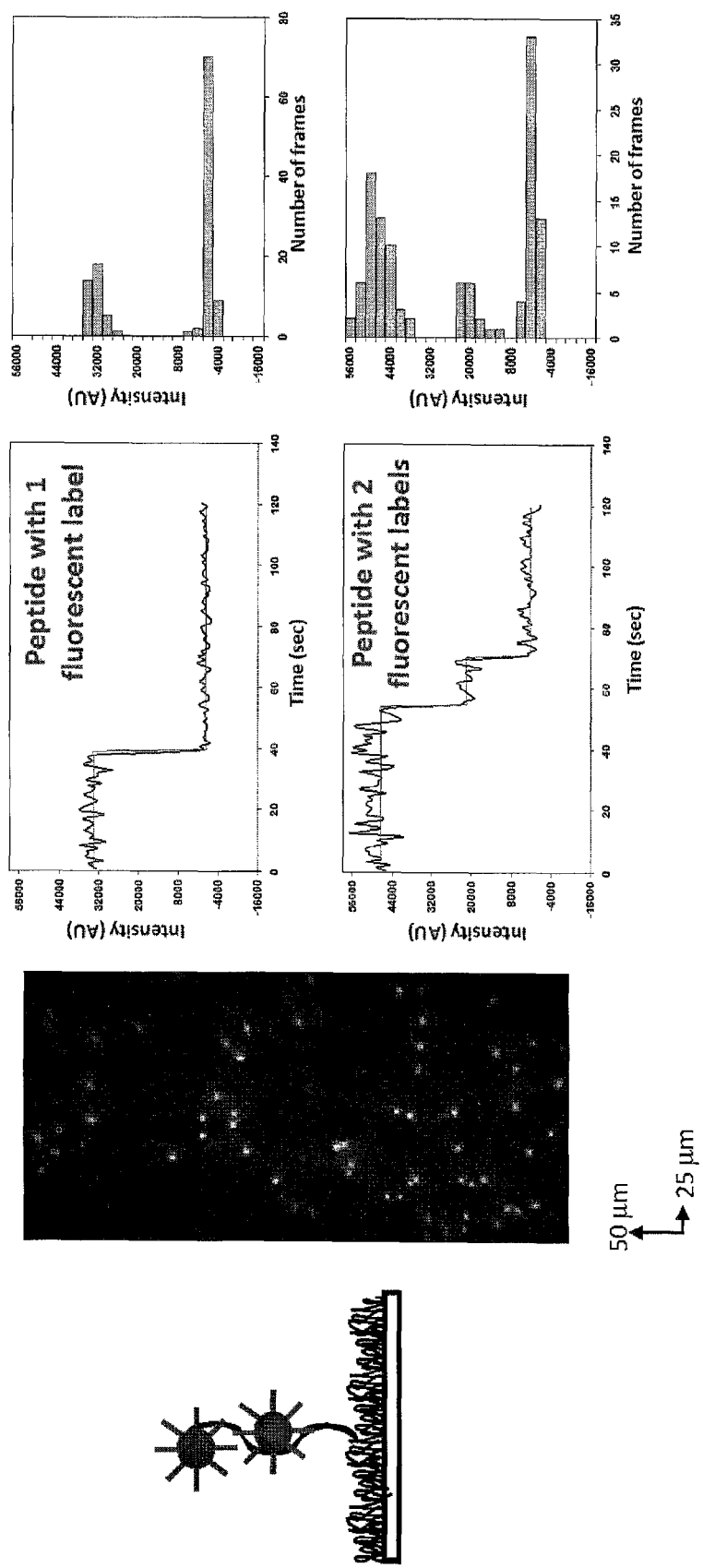
FIG. 13 shows one embodiment of peptides with labeled lysines (i.e. labeled with the amine-reactive dye HiLyte 647), said peptides attached by cysteines to maleimide-PEG quarts surface. The different pattern of fluorescence intensity with the different labeled lysine content. HiLyte Fluor™ 647 succidinimyl ester is a amine-reactive fluorescent labeling dye that generates the conjugates that are slightly red-shifted compared to those of Cy5 dyes, resulting in an optimal match to filters designed for Cy5 dye. Its conjugate may have better performance than Cy5 for fluorescence polarization-based assays.
Figure 14:
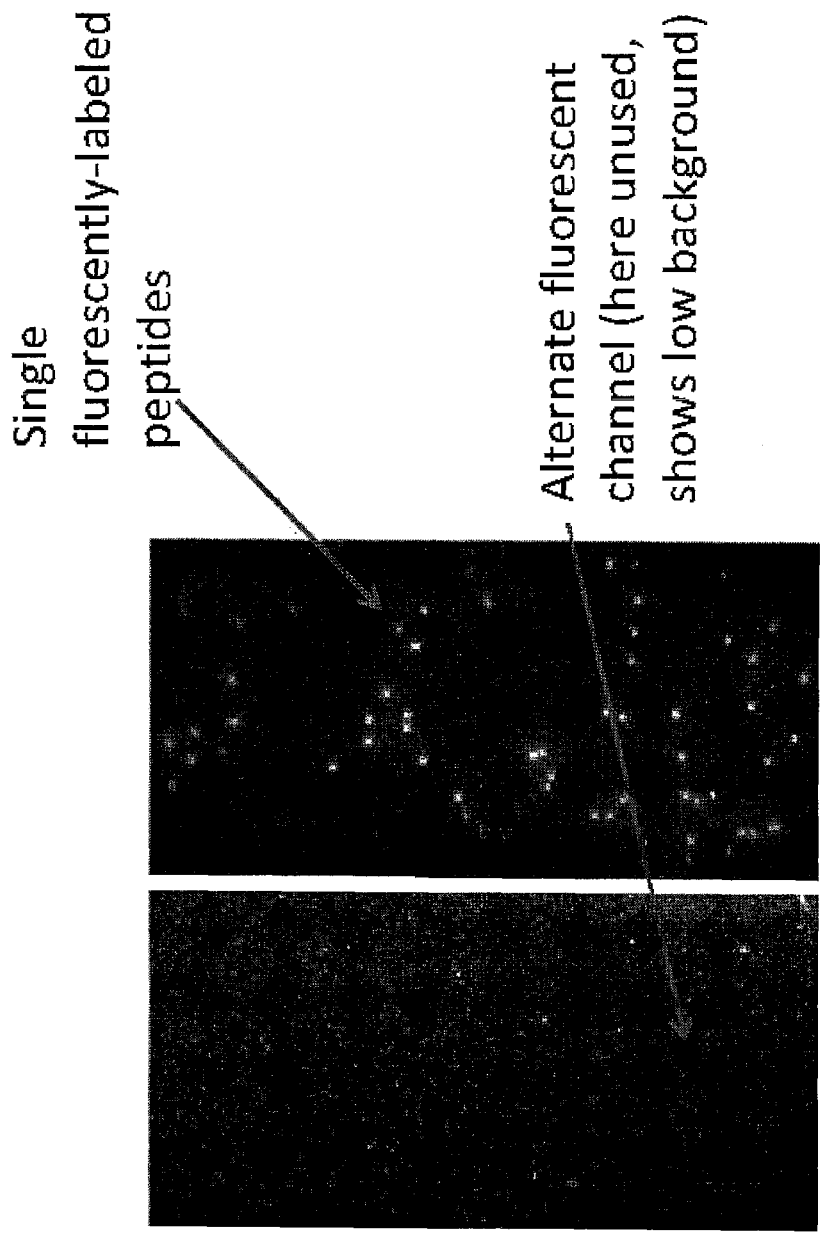
FIG. 14 shows a comparison of single fluorescently-labeled peptides and alternate channel revealing low background fluorescence.
Figure 15:
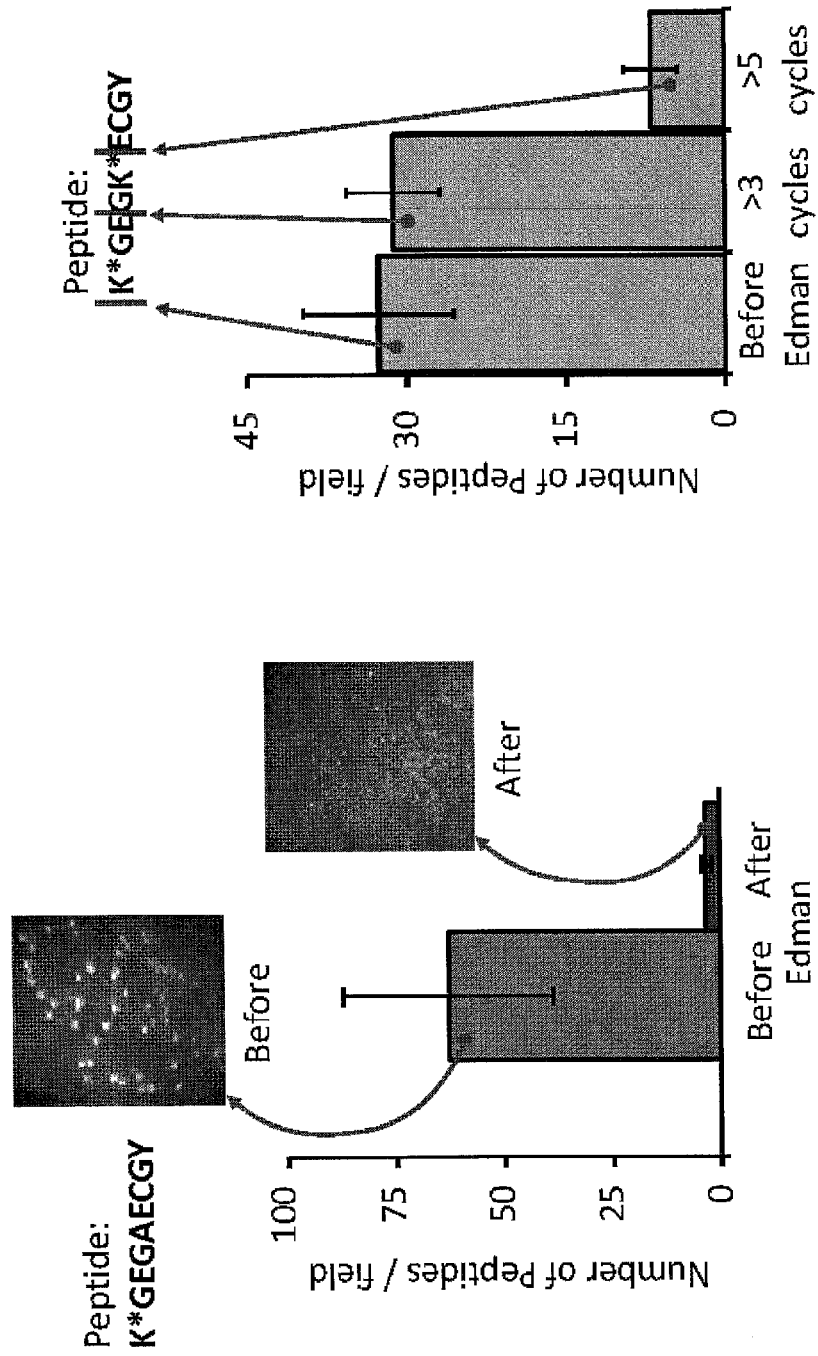
FIG. 15 shows the difference in the Edman degradation of the labeled single peptide molecules between a peptide that contains one versus two labeled lysines. The fluorescence signal drops when the labeled lysine is removed. Only fluorescence signal is found with labeled lysines.

The method has the ability to identify the location of peptides as well as the ability to follow these peptides after a number of steps. FIG. 13 shows one embodiment of labeled lysines (amine-reactive dye HiLyte 647) attached by cysteines to maleimide-PEG quartz surface. The different pattern of fluorescence intensity with the different labeled lysine content is revealed. The reactive dye used, HiLyte Fluor™ 647 succidinimyl ester, is an amine-reactive fluorescent labeling dye that generates the conjugates that are slightly red-shifted compared to those of Cy5 dyes, resulting in an optimal match to filters designed for Cy5 dye. Its conjugate may have better performance than Cy5 for fluorescence polarization-based assays. FIG. 14 shows a comparison of single fluorescently-labeled peptides and alternate channel revealing low background fluorescence. When analyzing the peptides, one can observe the difference in the Edman degradation of the labeled single peptide molecules between a peptide that contains one versus two labeled lysines (see FIG. 15). The fluorescence signal drops when the labeled lysine is removed. Only fluorescence signal is found with labeled lysines. One can also use quantum dots as a guide in analysis of large numbers of peptides from by scanning the microscope and tiling images (see FIG. 16).

A database of predicted potential proteins for the organism under investigation is used as a reference database. For example, in one embodiment the human protein database, compiled from the UniProt protein sequence database and containing 20,252 translated protein sequences, may be used as the reference dataset. A list of potential peptides is generated by simulating the proteolysis, labeling and anchoring approach used in the experiment. In the example provided above, this corresponds to cutting by GluC, labeling of lysines and anchoring of peptides via cysteines. Each unique peptide generated in this simulation may be transformed to its corresponding binary sequence (e.g. 0001000110), retaining its mapping to the protein sequence and ID from which it was formed. This creates a lookup database indexing potential binary sequences derived from that organism's proteome to unique protein IDs.

The binary intensity profile of each peptide, as generated from the single molecule microscopy, is then compared to the entries in the simulated peptide database (step 3). This provides the protein ID, if available, from which the peptide is uniquely derived. Performing this lookup over all measured profiles results in the identification of the set of proteins composing the complex protein mixture. Many binary intensity profiles may not have a unique match in the database. In one embodiment, advanced bioinformatics analyses could consider the multiplicity of matches and infer the most likely proteins present. In another embodiment, a simple approach is to just ignore all of these cases and rely only upon uniquely matching cases to build evidence for proteins being present. Quantitation is then accomplished by counting peptides derived from each protein observed. Since this approach is intrinsically digital, the count of peptides from each protein should be proportional to the abundance of the protein in the mixture. In another embodiment, the efficiencies of the reaction steps, including the labeling, Edman reagent coupling, and Edman reagent cleavage reactions can be measured or estimated and then incorporated in the computational search of the proteome sequences in order to provide a probabilistic estimate of the identification of a particular peptide or protein in the database.

f) Variations

Variants to the above protocol are contemplated. In one embodiment, to improve signal to noise during single molecule imaging, oxygen- and free radical-scavenging and triple quenching components are included in the solution (e.g., see Harris et al., Science 320, 106 (2008) [5], (herein incorporated by reference). In another embodiment, the surface of the solid support can be modified chemically, such as by coating with polyethylene glycol, in order to suppress nonspecific adsorption to the surface and thus improve the signal to noise ratio for the fluorescent detection of peptides. In another embodiment, more than two fluorescent molecules may be used to label additional amino acids. Such an approach might involve, for example, covalently labeling lysines with a fluorescent Edman reagent prior to sequencing (as described above) and also covalently labeling amino acids with carboxylate side chains (e.g., glutamate, aspartate) with a second fluorescent molecule (chosen for spectral compatibility), then proceeding with Edman degradation cycles using an Edman reagent labeled with a third fluorescent molecule. This method would provide more information-rich sequence profiles for identifying many more peptides. In another embodiment, an alternate imaging strategy involves the use of scanning confocal microscopy. In yet another embodiment, the cleavage/re-labeling steps of the Edman reaction are replaced with a protocol in which the re-labeling is performed using the Edman label 2 (as above), but then the cleavage step is performed using an aminopeptidase enzyme to remove the labeled amino-terminal amino acid. This would allow all reactions to be performed in aqueous solvent and simplify the apparatus by decreasing the need for organic solvents. In this embodiment, the aminopeptidase would be selected such that it requires and tolerates the presence of label 2 on the amino-terminal amino acid, therefore it would likely have to be optimized using in vitro evolution techniques to be suitable for use in sequencing.

In yet another embodiment, the successful removal of amino acids occurs from the carboxy terminus of the peptide, thereby revealing C-terminal sequences instead of N-terminal sequences. In a preferred embodiment, this approach employs, for example, engineered carboxypeptidases or small molecule reagents reacting analogous to the N-terminal Edman chemistry but operating from the C-terminus of the peptide.

REFERENCES

1. Edman et al. (1950) Method for determination of the amino acid sequence in peptides, *Acta Chem. Scand.* 4, 283-293.
2. Edman, P. and Begg, G. (1967) A Protein Sequenator, *Eur. J. Biochem.* 1(1), 80-91.
3. Niall, H. D. (1973) Automated Edman degradation: the protein sequenator, *Methods Enzymol.* 27, 942-1010.
4. Braslaysky, I. et al. (2003) Sequence information can be obtained from single DNA molecules, *Proc. Natl. Acad. Sci. U.S.A.* 100(7), 3960-3964.
5. Harris, T. D. et al. (2008) Single-Molecule DNA Sequencing of a Viral Genome, *Science* 320(5872), 106-109.

TABLE 1

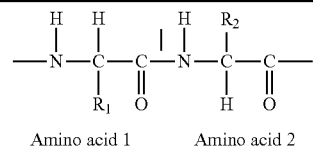

Amino acid 1      Amino acid 2

| Method | Peptide bonds cleaved |
|---|---|
| Trypsin | Amino acid 1 = Lys or Arg |
| Chymotrypsin | Amino acid 1 = Phe, Trp, or Tyr |
| Pepsin | Amino acid 1 = Phe, Trp, Tyr, and several others |
| Thermolysin | Amino acid 2 = Leu, Ile, or Val |
| Cyanogen bromide | Amino acid 1 = Met |

We claim:

1. A method of treating peptides, comprising:
   a) providing a plurality of peptides immobilized on a solid support, each peptide comprising an N-terminal amino acid and internal amino acids, said internal amino acids comprising lysine, each lysine labeled with a label, and said label producing a signal for each peptide;
   b) treating said plurality of immobilized peptides under conditions such that each N-terminal amino acid of each peptide is removed; and
   c) detecting the signal for each peptide at the single molecule level.

2. The method of claim 1, wherein said label is a fluorescent label.

3. The method of claim 1, wherein the removal in step b) said N-terminal amino acid of each peptide reacted with a phenyl isothiocyanate derivative.

4. The method of claim 1, wherein the removal of said N-terminal amino acid in step b) is done under conditions such that the remaining peptides each have a new N-terminal amino acid.

5. The method of claim 4, further comprising the step d) removing the next N-terminal amino acid done under conditions such that the remaining peptides each have a new N-terminal amino acid.

6. The method of claim 5, further comprising the step e) detecting the next signal for each peptide at the single molecule level.

7. The method of claim 6, wherein the N-terminal amino acid removing step and the detecting step are successively repeated from 1 to 20 times.

8. The method of claim 7, wherein the repetitive detection of signal for each peptide at the single molecule level results in a pattern.

9. The method of claim 8, wherein the pattern is unique to a single-peptide within the plurality of immobilized peptides.

10. The method of claim 9, wherein the single-peptide pattern is compared to the proteome of an organism to identify the peptide.

11. The method of claim 6, wherein the intensity of said labels are measured amongst said plurality of immobilized peptides.

12. The method of claim 1, wherein the N-terminal amino acids are removed in step b) by an Edman degradation reaction.

13. The method of claim 1, wherein the peptides are immobilized via cysteine residues.

14. The method of claim 1, wherein the detecting in step c) is done with optics capable of single-molecule resolution.

15. The method of claim 7, wherein the degradation step in which removal of the N-terminal amino acid coincides with removal of the label is identified.

16. The method of claim 15, wherein said removal of the amino acid is measured in step b) is measured as a reduced fluorescence intensity.

17. A method of treating peptides, comprising:
a) providing a plurality of peptides immobilized on a solid support, each peptide comprising an N-terminal amino acid and internal amino acids, said internal amino acids comprising lysine, each lysine labeled with a first label, said first label producing a first signal for each peptide, and said N-terminal amino acid of each peptide labeled with a second label, said second label being different from said first label;
b) treating said plurality of immobilized peptides under conditions such that each N-terminal amino acid of each peptide is removed; and
c) detecting the first signal for each peptide at the single molecule level.

18. The method of claim 17, wherein said second label is attached via an amine-reactive dye.

19. The method of claim 18, wherein said second label is selected from the group consisting of fluorescein isothiocyanate, rhodamine isothiocyanate or other synthesized fluorescent isothiocyanate derivative.

20. The method of claim 17, wherein portions of the emission spectrum of said first label do not overlap with the emission spectrum of said second label.

21. The method of claim 17, wherein the removal of said N-terminal amino acid in step b) is done under conditions such that the remaining peptides each have a new N-terminal amino acid.

22. The method of claim 21, further comprising the step d) adding said second label to said new N-terminal amino acids of the remaining peptides.

23. The method of claim 22, wherein among the remaining peptides the new end terminal amino acid is lysine.

24. The method of claim 22, further comprising the step e) detecting the next signal for each peptide at the single molecule level.

25. The method of claim 24, wherein the N-terminal amino acid removing step, the detecting step, and the label adding step to a new N-terminal amino acid are successively repeated from 1 to 20 times.

26. The method of claim 25, wherein the repetitive detection of signal for each peptide at the single molecule level results in a pattern.

27. The method of claim 26, wherein the pattern is unique to a single-peptide within the plurality of immobilized peptides.

28. The method of claim 27, wherein the single-peptide pattern is compared to the proteome of an organism to identify the peptide.

29. The method of claim 24, wherein the intensity of said first and second labels are measured amongst said plurality of immobilized peptides.

30. The method of claim 17, wherein the N-terminal amino acids are removed in step b) by an Edman degradation reaction.

31. The method of claim 17, wherein the peptides are immobilized via cysteine residues.

32. The method of claim 17, wherein the detecting in step c) is done with optics capable of single-molecule resolution.

33. The method of claim 23, wherein the degradation step in which removal of second label coincides with removal of first label is identified.

34. The method of claim 33, wherein said removal of the amino acid is measured in step b is measured as a reduced fluorescence intensity.

35. A method of identifying amino acids in peptides, comprising:
a) providing a plurality of peptides immobilized on a solid support, each peptide comprising an N-terminal amino acid and internal amino acids, said internal amino acids comprising lysine, each lysine labeled with a first label, said first label producing a first signal for each peptide, and said N-terminal amino acid of each peptide labeled with a second label, said second label being different from said first label, wherein a subset of said plurality of peptides comprise an N-terminal lysine having both said first and second label;
b) treating said plurality of immobilized peptides under conditions such that each N-terminal amino acid of each peptide is removed; and
c) detecting the first signal for each peptide at the single molecule level under conditions such that said subset of peptides comprising an N-terminal lysine having both said first and second label is identified.

36. The method of claim 35, wherein the removal of said N-terminal amino acid in step b) is done under conditions such that the remaining peptides each have a new N-terminal amino acid.

37. The method of claim 35, wherein the N-terminal amino acids are removed in step b) by an Edman degradation reaction.

38. The method of claim 35, wherein the peptides are immobilized via cysteine residues.

39. A method of identifying amino acids in peptides, comprising:
a) providing a plurality of peptides immobilized on a solid support, each peptide comprising an N-terminal amino acid and internal amino acids, said internal amino acids comprising lysine, each lysine labeled with a first label, said first label producing a first signal for each peptide, and said N-terminal amino acid of each peptide labeled with a second label, said second label being different from said first label, wherein a subset of said plurality of peptides comprise an N-terminal acid that is not lysine;
b) treating said plurality of immobilized peptides under conditions such that each N-terminal amino acid of each peptide is removed; and
c) detecting the first signal for each peptide at the single molecule level under conditions such that said subset of peptides comprising an N-terminal amino acid that is not lysine is identified.

40. The method of claim 39, wherein the removal of said N-terminal amino acid in step b) is done under conditions such that the remaining peptides each have a new N-terminal amino acid.

41. The method of claim 39, wherein the N-terminal amino acids are removed in step b) by an Edman degradation reaction.

42. The method of claim 39, wherein the peptides are immobilized via cysteine residues.

43. A method of generating and treating peptides, comprising:
a) digesting a protein preparation with an agent that cleaves after a specific amino acid residue so as to generate a plurality of peptides, each peptide comprises an N-terminal amino acid and internal amino acids, at least a portion of said internal amino acids of said peptides comprising lysine, at least a portion of said peptides comprising said specific amino acid residue at the C-terminus;
b) labeling said plurality of peptides such that each lysine is labeled with a label, said label producing a signal for each peptide;
c) immobilizing said labeled peptides on a solid support;
d) treating said plurality of immobilized peptides under conditions such that each N-terminal amino acid of each peptide is removed; and
e) detecting the signal for each peptide at the single molecule level.

44. The method of claim 43, wherein said agent is an enzyme.

45. The method of claim 44, wherein said enzyme is a specific endopeptidase.

46. The method of claim 45, wherein said endopeptidase is peptidase GluC.

47. The method of claim 43, wherein said agent is a chemical agent.

48. The method of claim 47, wherein said chemical agent is cyanogen bromide.

49. The method of claim 43, wherein said label is a fluorescent label.

50. The method of claim 43, wherein the removal in step d) said N-terminal amino acid of each peptide reacted with a phenyl isothiocyanate derivative.

51. The method of claim 43, wherein the removal of said N-terminal amino acid in step d) is done under conditions such that the remaining peptides each have a new N-terminal amino acid.

52. The method of claim 51, further comprising the step f) removing the next N-terminal amino acid done under conditions such that the remaining peptides each have a new N-terminal amino acid.

53. The method of claim 52, further comprising the step g) detecting the next signal for each peptide at the single molecule level.

54. The method of claim 53, wherein the N-terminal amino acid removing step and the detecting step are successively repeated from 1 to 20 times.

55. The method of claim 54, wherein the repetitive detection of signal for each peptide at the single molecule level results in a pattern.

56. The method of claim 8, wherein the pattern is unique to a single-peptide within the plurality of immobilized peptides.

57. The method of claim 9, wherein the single-peptide pattern is compared to the proteome of an organism, using said specific amino acid residue at the C-terminus, to identify the peptide.

* * * * *

UNITED STATES PATENT AND TRADEMARK OFFICE
CERTIFICATE OF CORRECTION

PATENT NO. : 9,625,469 B2
APPLICATION NO. : 14/128247
DATED : April 18, 2017
INVENTOR(S) : Marcotte et al.

Page 1 of 1

It is certified that error appears in the above-identified patent and that said Letters Patent is hereby corrected as shown below:

In the Specification

Column 1, Line 7-12 should read:
This invention was made with government support under Grant no. R01 GM088624 and Grant no. GM106408 awarded by the National Institutes of Health. The government has certain rights in the invention.

Signed and Sealed this
Thirtieth Day of May, 2017

Michelle K. Lee
*Director of the United States Patent and Trademark Office*